United States Patent [19]
Pohlenz et al.

[11] Patent Number: 5,543,306
[45] Date of Patent: Aug. 6, 1996

[54] PROCESS FOR THE ISOLATION AND CHARACTERISATION OF A GENE ENZYME SYSTEM FOR INACTIVATION OF THE HERBICIDE PHENMEDIPHAM AND TRANSFER OF THE GENE INTO PLANTS

[75] Inventors: Hans-Dieter Pohlenz; Werner Boidol; Wolfgang Streber, all of Berlin, Germany

[73] Assignee: Schering Aktiengesellschaft, Germany

[21] Appl. No.: 196,361

[22] Filed: Feb. 14, 1994

Related U.S. Application Data

[60] Division of Ser. No. 615,448, Nov. 19, 1990, Pat. No. 5,347,076, which is a continuation-in-part of Ser. No. 358,871, May 18, 1989, abandoned.

[30] Foreign Application Priority Data

May 19, 1988 [DE] Germany ................. 38 17 384.0

[51] Int. Cl.$^6$ ................. C12N 15/82; C12N 15/31; C12N 15/55; C12N 15/67
[52] U.S. Cl. ................. 435/91.41; 536/23.2; 536/24.2; 536/24.1; 435/320.1
[58] Field of Search ................. 536/23.2, 23.7, 536/24.3, 24.32, 24.33, 24.1, 24.2; 435/320.1, 172.3, 91.41, 91.5

[56] References Cited

U.S. PATENT DOCUMENTS 4,810,648  3/1989  Stalker ................. 435/240.1

OTHER PUBLICATIONS

C. O. Knowles, et al. "Microbial Degradation of the Carbamate Pesticides Desmedipham, Phenmedipham, Promecarb, and Propamocarb", *Bull. Environm. Contam. Toxicol.*, 27, 529–533 (1981).

David N. Radin, et al. "Herbicide–tolerant tobacco mutants selected *in situ* and recovered via regeneration from cell structure" *Genet. Res. Camb.*, (1978), 32, pp. 85–89.

Knowles, et al. Bull. Environ. Contam. Toxicol. 27: 529–533 (1981).

*Primary Examiner*—Che S. Chereskin
*Attorney, Agent, or Firm*—Ostrolenk, Faber, Gerb & Soffen

[57] ABSTRACT

A process for the isolation and characterization of a gene enzyme system for the inactivation of the herbicide phenmedipham, wherein the enzyme is a carbamate hydrolase of *Arthrobacter oxidans*, which is responsible for the cleavage of the carbamate bond between the benzene rings of phenmedipham. This process includes the isolation of the carbamate hydrolase, the identification of the amino acid sequence of two BrCN cleavage peptides of the carbamate hydrolase, the synthesis of oligonucleotides for specific determination of the carbamate hydrolase sequence by hybridization and identification of the coding region, cloning and specifying the nucleotide sequence of the carbamate hydrolase gene from *Arthrobacter oxidans*.

5 Claims, 17 Drawing Sheets

```
                    870                    900
GACCCGAACCGGATCACTCTCGTCGGTCAATCAGGCGGGGCATACTCGATCGCAGCGCTC
AspProAsnArgIleThrLeuValGlyGlnSerGlyGlyAlaTyrSerIleAlaAlaLeu 930                    960
GCCCAACACCCGGTCGCCCGTCAGCTGTTCCACCGCGCGATCCTACAAAGCCCACCATTC
AlaGlnHisProValAlaArgGlnLeuPheHisArgAlaIleLeuGlnSerProProPhe 990                   1020
GGGATGCAACCCCATACAGTTGAAGAATCGACGGCAAGGACGAAGGCCCTGGCCCGGCAT
GlyMetGlnProHisThrValGluGluSerThrAlaArgThrLysAlaLeuAlaArgHis 1050                   1080
CTCGGGCACGATGACATCGAGGCCCTGCGCCATGAGCCGTGGGAGAGGCTGATTCAAGGC
LeuGlyHisAspAspIleGluAlaLeuArgHisGluProTrpGluArgLeuIleGlnGly 1110                   1140
ACGATAGGCGTCCTGATGGAACACACCAAATTTGGCGAATGGCCCCTGGCATTCTATCCG
ThrIleGlyValLeuMetGluHisThrLysPheGlyGluTrpProLeuAlaPheTyrPro
                                          Oligo III 1170                   1200
GTGTTCGATGAGGCAACGATACCTCGCCATCCGATTGAGTCCATTATCGATTCCGACATC
ValPheAspGluAlaThrIleProArgHisProIleGluSerIleIleAspSerAspIle 1230                   1260
GAAATCATCATCGGCTGGACACGCGACGAGGGCACTTTTCCGTTTGCCTTCGACCCTCAG
GluIleIleIleGlyTrpThrArgAspGluGlyThrPheProPheAlaPheAspProGln 1290                   1320
GTTTCACAGGCGGATCGCGATCAGGTCGAGTCATGGTTGCAGAAGCGTTTCGGAGACCAC
ValSerGlnAlaAspArgAspGlnValGluSerTrpLeuGlnLysArgPheGlyAspHis 1350                   1380
GCCGCCTCGGCCTACGAGGCTCACGCCGGCGACGGAACCAGTCCTTGGACCGTTATCGCC
AlaAlaSerAlaTyrGluAlaHisAlaGlyAspGlyThrSerProTrpThrValIleAla 1410                   1440
AACGTTGTGGGCGACGAGCTCTTTCACAGCGCTGGGTACCGGGTCGCGGACGAACGGGCA
AsnValValGlyAspGluLeuPheHisSerAlaGlyTyrArgValAlaAspGluArgAla 1470                   1500
ACGCGCAGACCGGTACGGGCCTATCAGTTCGACGTAGTCTCGCCCTTGTCGGACGGAGCC
ThrArgArgProValArgAlaTyrGlnPheAspValValSerProLeuSerAspGlyAla 1530                   1560
CTCGGCGCGGTCCACTGCATCGAAATGCCGTTCACATTTGCCAATCTCGACCGTTGGACG
LeuGlyAlaValHisCysIleGluMetProPheThrPheAlaAsnLeuAspArgTrpThr
                                         Oligo I & II 1590                   1620
GGGAAGCCGTTCGTGGACGGCCTGGATCCAGACGTGGTGGCTCGGGTGACCAACGTGTTG
GlyLysProPheValAspGlyLeuAspProAspValValAlaArgValThrAsnValLeu
```

FIG. 7A

```
                    .              .          1650             .              .          1680
          CATCAGGCCTGGATCGCATTCGTCCGAACGGGAGACCCCACGCACGACCAGTTGCCGGTG
          HisGlnAlaTrpIleAlaPheValArgThrGlyAspProThrHisAspGlnLeuProVal

.              .          1710             .              .          1740
          TGGCCAACGTTCCGAGCGGACGACCCAGCGGTGTTGGTCGTCGGCGACGAGGGAGCAGAG
          TrpProThrPheArgAlaAspAspProAlaValLeuValValGlyAspGluGlyAlaGlu

.              .          1770             .              .          1800
          GTGGCGCGGGATCTAGCGCGCCCGGACCACGTCAGCGTTCGGACCCTATGAGGGTCGCGG
          ValAlaArgAspLeuAlaArgProAspHisValSerValArgThrLeu

.              .          1830             .              .          1860
          GTCGCCGGGGTCTTGAGGCCGGAGGGCCTCGCGTATGCAGTGATTCGTGGATCACCGGCC

AGTT
```

FIG. 7B

PROCESS FOR THE ISOLATION AND CHARACTERISATION OF A GENE ENZYME SYSTEM FOR INACTIVATION OF THE HERBICIDE PHENMEDIPHAM AND TRANSFER OF THE GENE INTO PLANTS

This application is a divisional of U.S. Ser. No. 07/615,448 filed Nov. 19, 1990, now U.S. Pat. No. 5,347,076, which is a continuation-in-part of U.S. Ser. No. 07/353,871, filed on May 18, 1989, now abandoned.

The present invention relates to a process for the isolation and characterisation of a gene enzyme system for the inactivation of the herbicide phenmedipham and transfer of the gene into plants to produce herbicide-tolerant plants. The enzyme is a carbamate hydrolase of *Arthrobacter oxidans*, which is responsible for the cleavage of the carbamate bond between the benzene rings of phenmedipham which is the common name for the herbicide methyl 3-m-tolycarbamoyloxyphenyl-carbamate.

In practice it is often necessary to use several herbicides or herbicide mixtures to combat various weeds. These problems can be avoided by a biotechnical change to the plant in which resistance to a non-selective herbicide is introduced.

The production of herbicide-tolerant plants is now coming more to the foreground in the plant protection area.

In order to produce herbicide-tolerant plants, it is necessary first to have a process the isolation and subsequent purification of an enzyme which is able to inactivate a herbicide, eg by metabolism, and then to have a process for characterising the gene enzyme system containing the DNA sequence that codes for the active enzyme. After these steps the DNA sequence of the gene can be transferred into plants.

Such a process for the isolation and subsequent characterisation of a gene enzyme system which can inactivate phenmedipham and the transfer of this gene enzyme system into plants was not previously known.

It has now been found that a carbamate hydrolase can be isolated from some microorganisms, such as *Arthrobacter oxidans*, which is responsible for the hydrolysis of the carbamate bond between the two benzene rings of phenmedipham. The hydrolysis of this bond leads to herbicidally inactive compounds such as methyl 3-hydroxyphenylcarbamate and meta-toluidine, according to the following reaction:

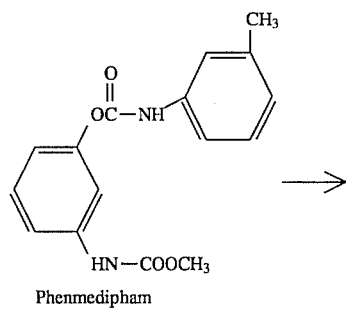

Phenmedipham

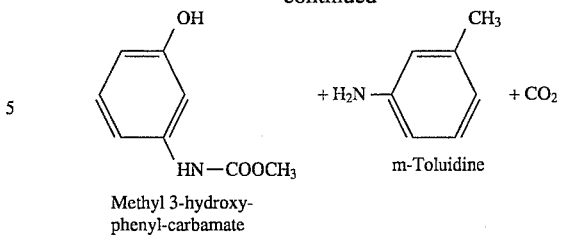

Methyl 3-hydroxy-phenyl-carbamate    m-Toluidine

For isolation and subsequent purification of a gene enzyme system which can hydrolyse phenmedipham according to the above described reaction, microorganism of *Arthrobacter oxidans* are cultivated in a nutrient medium. The carbamate hydrolase responsible for the cleavage of phenmedipham is isolate by ultrasound cell destruction, centrifugation and purification by anion exchange chromalography, gradient elution, ammonium sulphate precipitation and FPLC separation until electrophoretic homogeneity is achieved. From the purified carbamate hydrolase, two peptides are isolated after BrCN cleavage whose sequence can be estimated by Edman degradation. According to the sequence information of these peptides, oligonucleotides can be synthesised which can be used as hybridization in probes for the detection of the carbamate hydrolase gene.

In all of the mentioned isolates of the soil bacteria *Arthrobacter oxidans*, plasmids could be detected after lysis of the cells and extraction of the nucleic acids.

For the species *Arthrobacter oxidans* P52, it can be shown that the carbamate hydrolase is coded by one plasmid.

With the loss of the plasmic pHP52 the properties of this species to be able to hydrolytically cleave phenmedipham is lost. Carbamate hydrolysis activity cannot be biochemically established in the plasmid-free derivative of the species p52.

The plasmid pHP52 can be preparatively isolate and mapped with restriction endonucleases. The electrophoretically separated restriction fragments can be transferred onto membrane filters and hydrodised with various oligonucleotides. From the data from the blot-hybridisations, it appears that the carbamate hydrolase gene is localised on a PstI restriction fragment with a size of 3.3 kb.

This fragment can be preparatively isolated from the plasmid pHP52 and inserted in the PstI position of the vector pUC19C (Yanish-Perron, C., Vieira, J. & Messing (1985) Gene 33, 103 ff). After transformation of *E. coli* DH5α with the ligation preparation, two types of recombinant *E. coli* clones are obtained (pp52Pst and pp52Pst inv.) which contain the carbamate hydrolase gene in different orientations to the Lac promoter of the vector (see FIG. 5).

The carbamate hydrolase can be functionally expressed in the presence of the inducer isopropyl-β-D-thiogalactopyranoside from cultures of the clone of the type *E. coli* DH5α (pp52Pst). In protein extracts of clones of the type *E. coli* DH5α (pp52 inc.) which contain the carbamate hydrolase gene in inverse orientation to the Lac promoter, no expression of the carbamate hydrolase gene can be detected.

The nucleotide sequence of the carbamate hydrolase gene can be determined according to the method of Sanger et al. (Sanger, F., Nicklen, S. & Coulson, A (1977), Proc. Natl. Acad. Sci. USA 74, 5463–5468).

15 sub-clones arising from the cloning of 3.3 kb long PstI restriction fragments can be constructed in the single strain DNA bacteriophages M13 mp 18 and mp 19 (Messing, ] (1983) Methods in Enzymol. 101, 20–78). In FIG. 6 an exact restriction map of the coded area is represented from which the sequencing strategy can be seen.

The established nucleotide sequence (SEQ ID NO: 7) with the protein sequence thus derived is illustrated in FIGS.

7, 7A and 7B (SEQ ID NO: 6). The amino acid sequences of both established BrCN-splitting peptides (see Example 4) can b identified in the same reading frame as the DNA level. This reading frame ends with a TGA translation stop codon (see FIG. 7, 7A and 7B, (SEQ ID NO: 6) nucleotide positions 1789–1791) and begins very probably with a GTG-start codon (FIGS. 7, 7A and 7B (SEQ ID NO: 6)—nucleotide positions 310–312. Altogether a reading frame of 1479 base pairs results. Upstream of the putative GTG-start codon, a region with significant homology to the consensus sequence for *E. coli* ribosome binding sites ("Shine-Dalgarno Box") can be established (see FIGS. 7, 7A and 7B, (SEQ ID NO: 6) nucleotide positions 298–302).

After the nucleotide sequence of the carbamate hydrolase gene has been determined, the construction of plasmids for the expression of carbamate hydrolase in plants can be carried out (see Example 9). For this the chimeric carbamate hydrolase gene on plasmids can be transferred from *E. coli* to *Agrobacterium tumefaciens* and from *Agrobacterium tumefaciens* to the target plants (see Example 10). The operation of the carbamate hydrolase gene in transformed plants can be shown by spraying transformed and untransformed plants with phenmedipham (see Examples 11 and 12).

On the 25th Aug. 1987 the following micro-organisms were deposited at the German Collection of Microorganisms (DSM) in Göttingen, Germany.

| Arthrobacter oxidans | P 16/4/B | (DSM 4038) |
| Arthrobacter oxidans | P 67 | (DSM 4039) |
| Arthrobacter oxidans | P 75 | (DSM 4040) |
| Arthrobacter oxidans | P 11/1/-b | (DSM 4041) |
| Arthrobacter oxidans | P 15/4/A | (DSM 4045) |
| Arthrobacter oxidans | P 21/2 | (DSM 4046) |
| Arthrobacter oxidans | P 52. containing the plasmid pHP52 | (DSM 4044). |

Abbreviations

DEAE Diethylaminoethyl

FPLC Fast protein/peptide/polynucleotide liquid Chromatography

SDS Sodium lauryl sulphate

DTT Dithiothreitol

1×SSC 0.15M NaCl 0.015M trisodium citrate pH 7.0

1×Denhardt 0.02% (w/v) Bovine serum albumin (Sigma, Fraction V) 0.02% (w/v) Ficoll 400 0.02% polyvinylpyrrolidone MCS Multiple cloning site Abbreviation for Restriction Endonucleases Bm=BamHI, Bs=BstEII, Cl=ClaI, EV=EcoRV, HII=HindII, Kp=KpnI, Nc=NcoI, Nd=NdeI, Nh=NheI, Ps=PstI, PvI= PvuI, PvII=PvuII, Sc=SacI, Sp=SphI, St=StuI, Xb=XbaI.

A: Crude extract from the centrifuge supernatant of the ultrasound cell destruction of *Arthrobacter oxidans*.

B: Pooled protein fraction after gradient elution on a DEAE Sephacel column.

C: Ammonium sulphate precipitation of the fraction from B.

D: Protein fraction after gel filtration of the ammonium sulphate precipitation and subsequent separation on a Sephacryl S-300 column.

E: Protein fraction after separation of the pooled fraction from D by FPLC (anion exchange chromatography).

F: Protein fraction after separation of the pooled fraction E on a Superose 6 column (Example 2).

Figure 1:
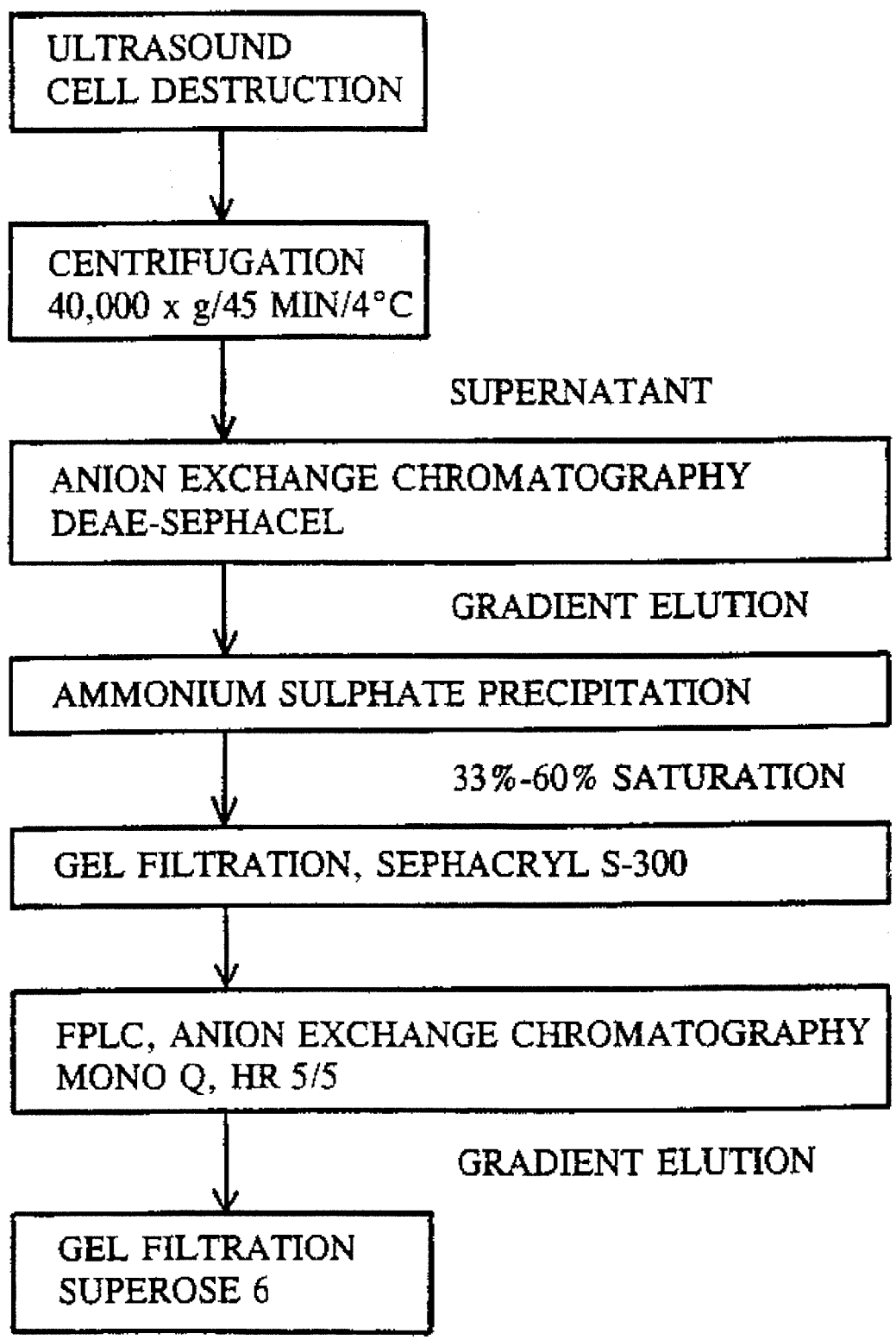
FIG. 1 shows the process for isolating and subsequent purification of phenmedipham cleaving carbamate hydrolase from *Arthrobacter oxidans* (Example 2).
Figure 2:
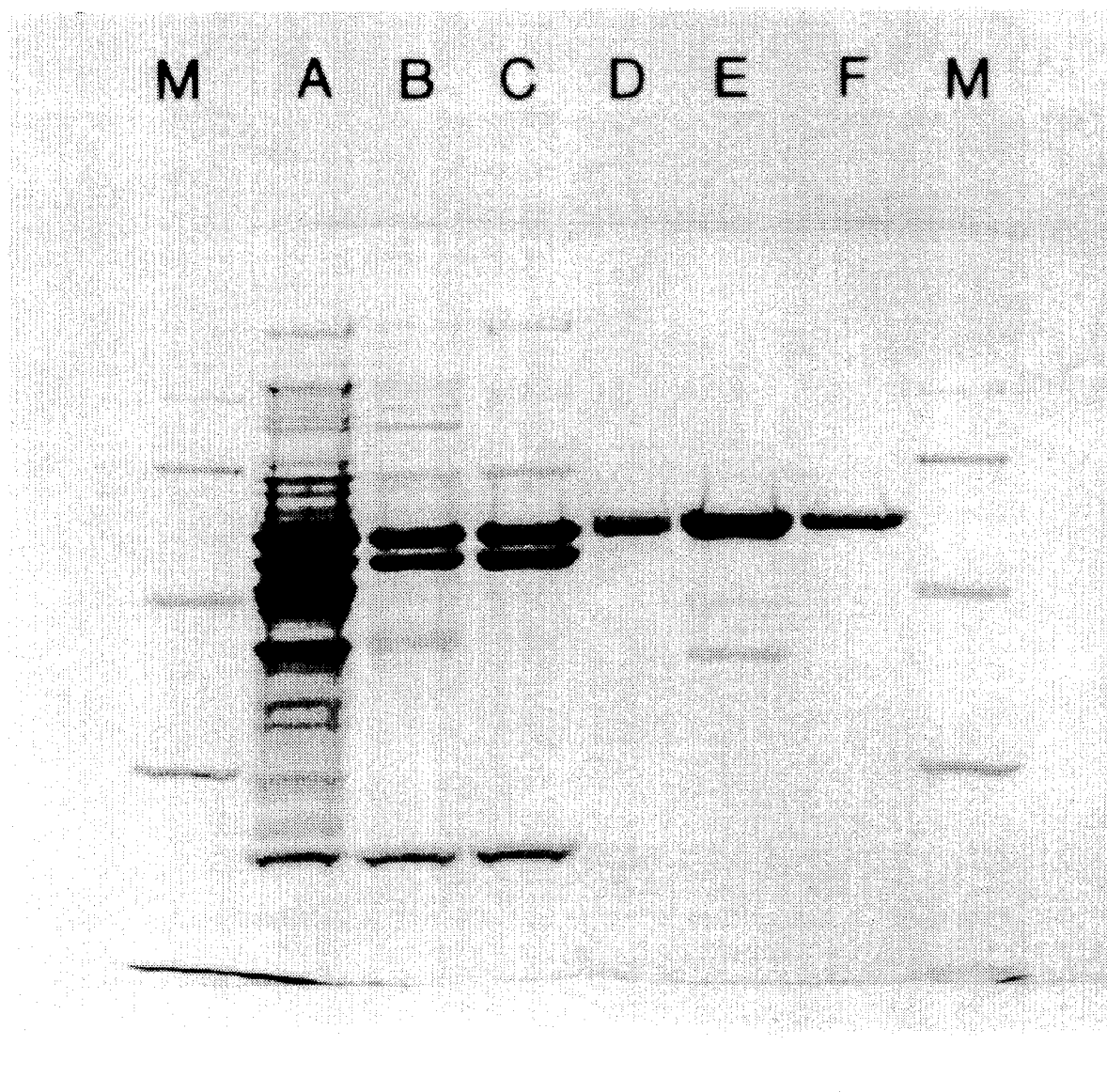
FIG. 2 shows the electrophoretic separation of the crude extract and the isolation and pooled protein fractions after the individual purification steps on an SDS-polyacrylamide gel, in which standard proteins (M) run alongside as markers for the molecular weight.
Figure 3:
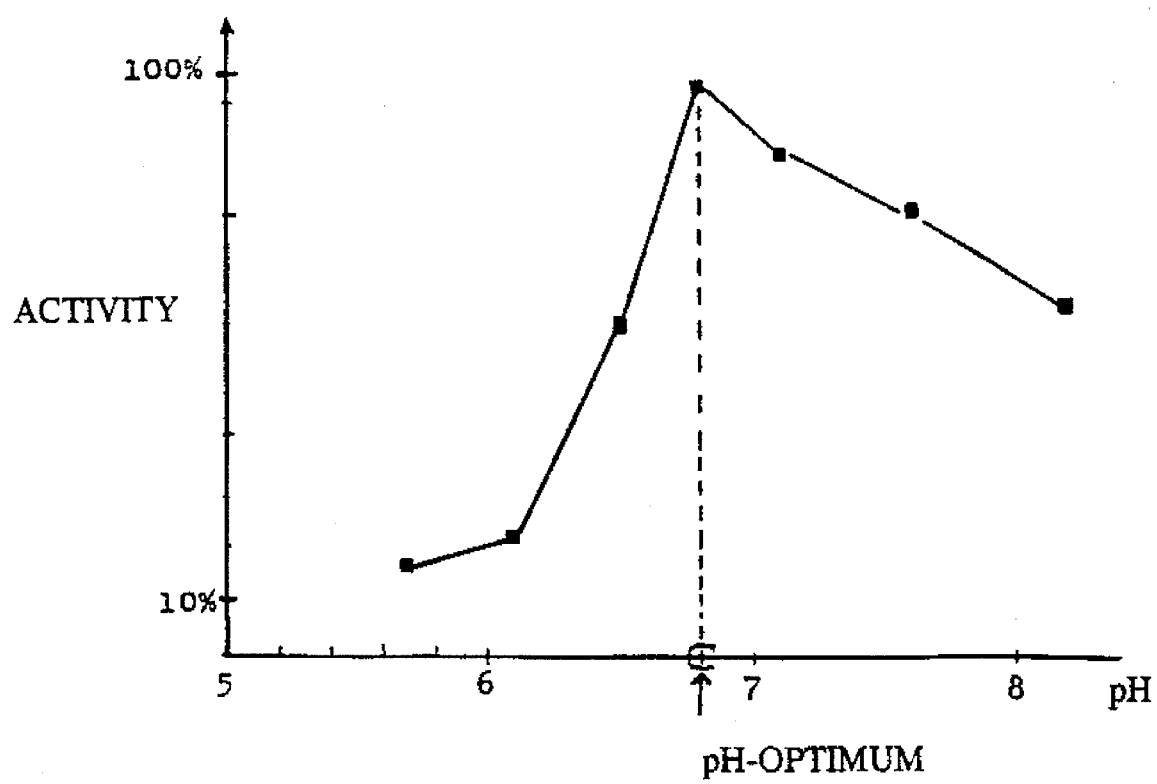

FIG. 3 shows a diagram from which the pH-optimum (pH 6.8) of the carbamate hydrolase can be obtained. The pH optimum can be established in such a way that the enzyme activity as a percentage against the pH value can be derived (Example 2).

Figure 4:
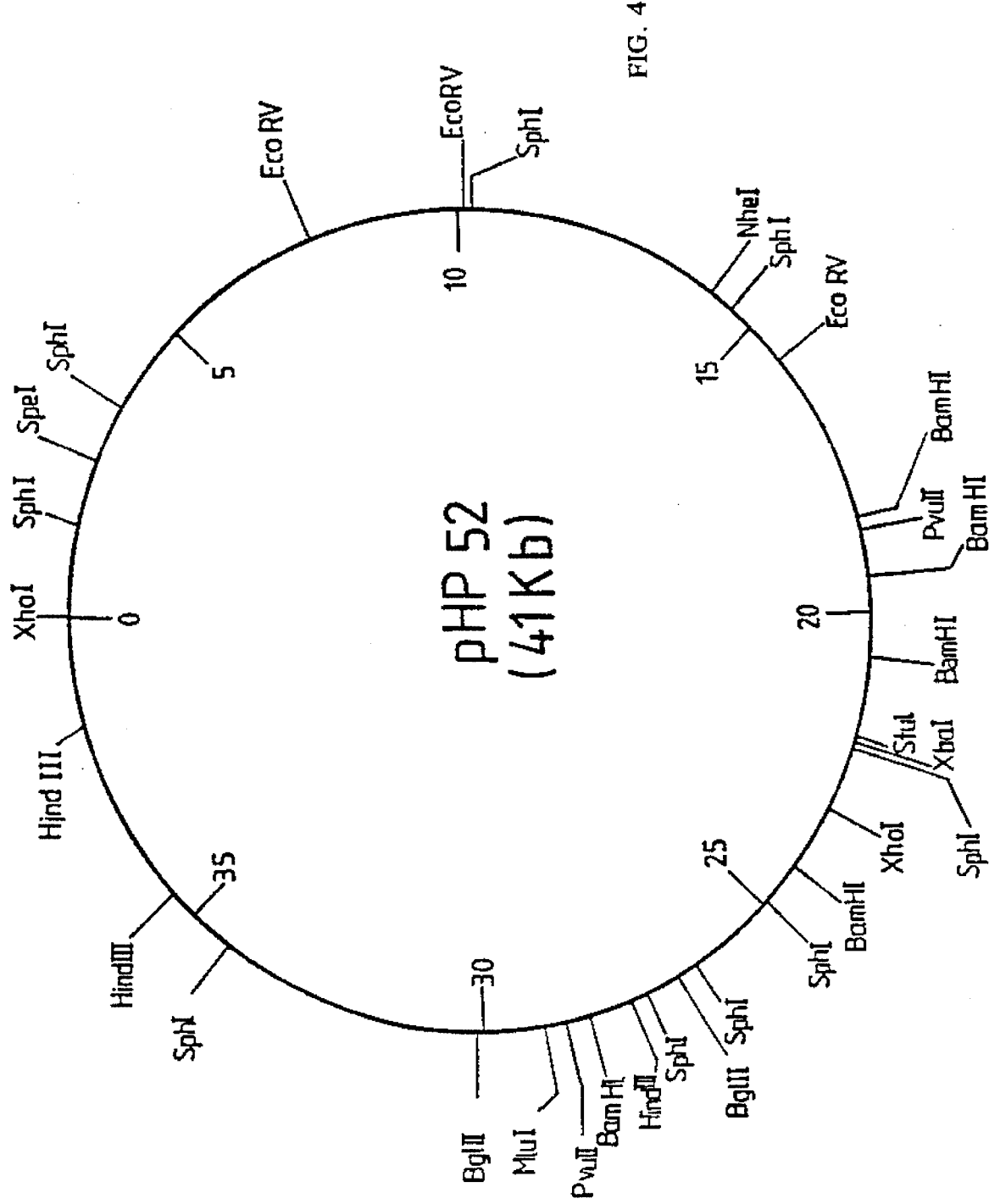

FIG. 4 shows the restriction map of the plasmid pHP52 from the *Arthrobacter oxidans* (species P52).

Figure 5:
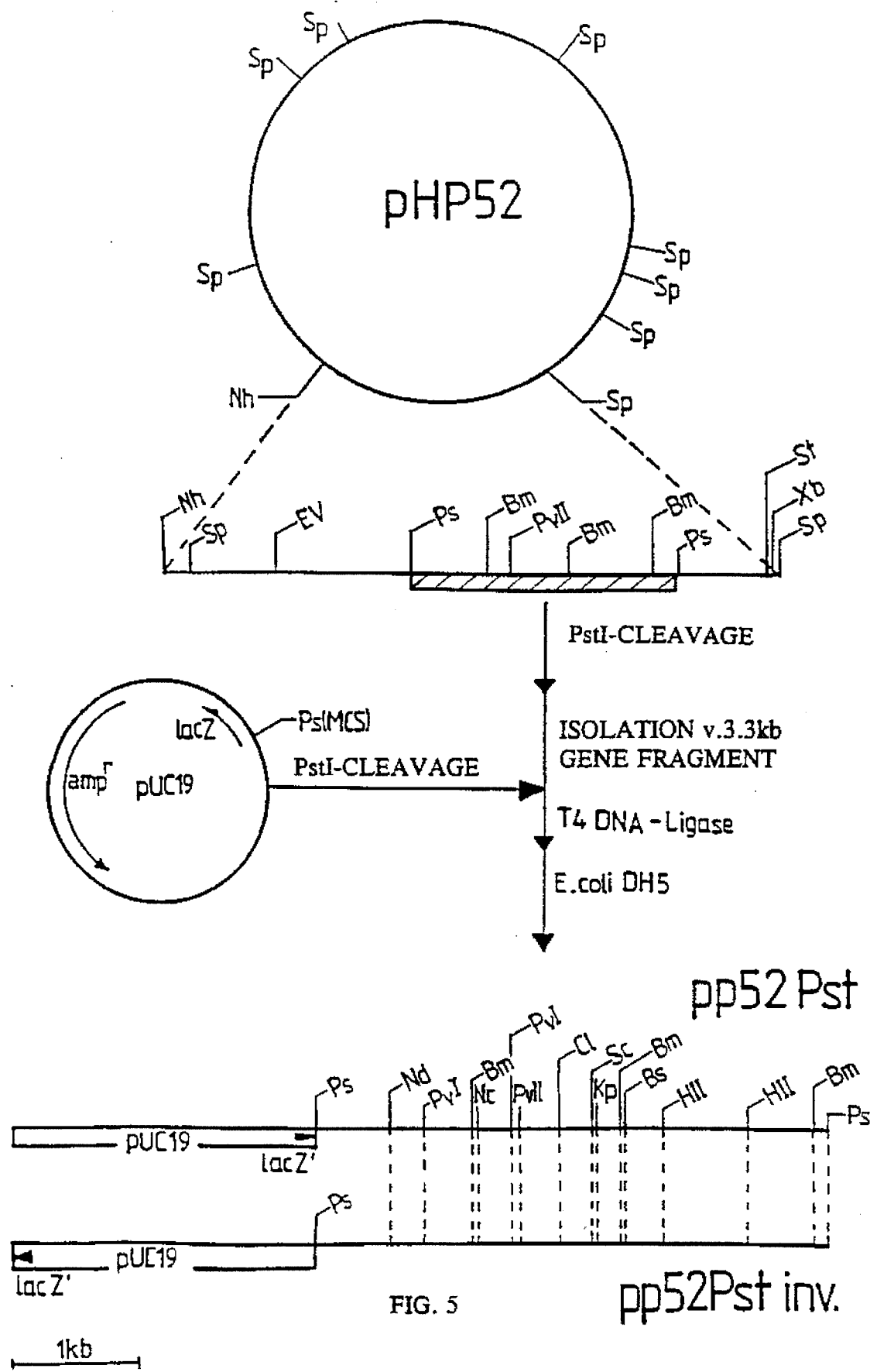

FIG. 5 shows a scheme of cloning of the carbamate hydrolase gene. To improve clarity, the regions of the gene which hybridine with oligonucleotides used including the 5' and 3' flanking regions are enlarged above the ring-formed plasmid map.

The recombinant clones pp52Pst and pp52Pst inv. are represented in a linear manner. The transcription direction of the lac Z gene is represented by an arrow. (>).

Figure 6:
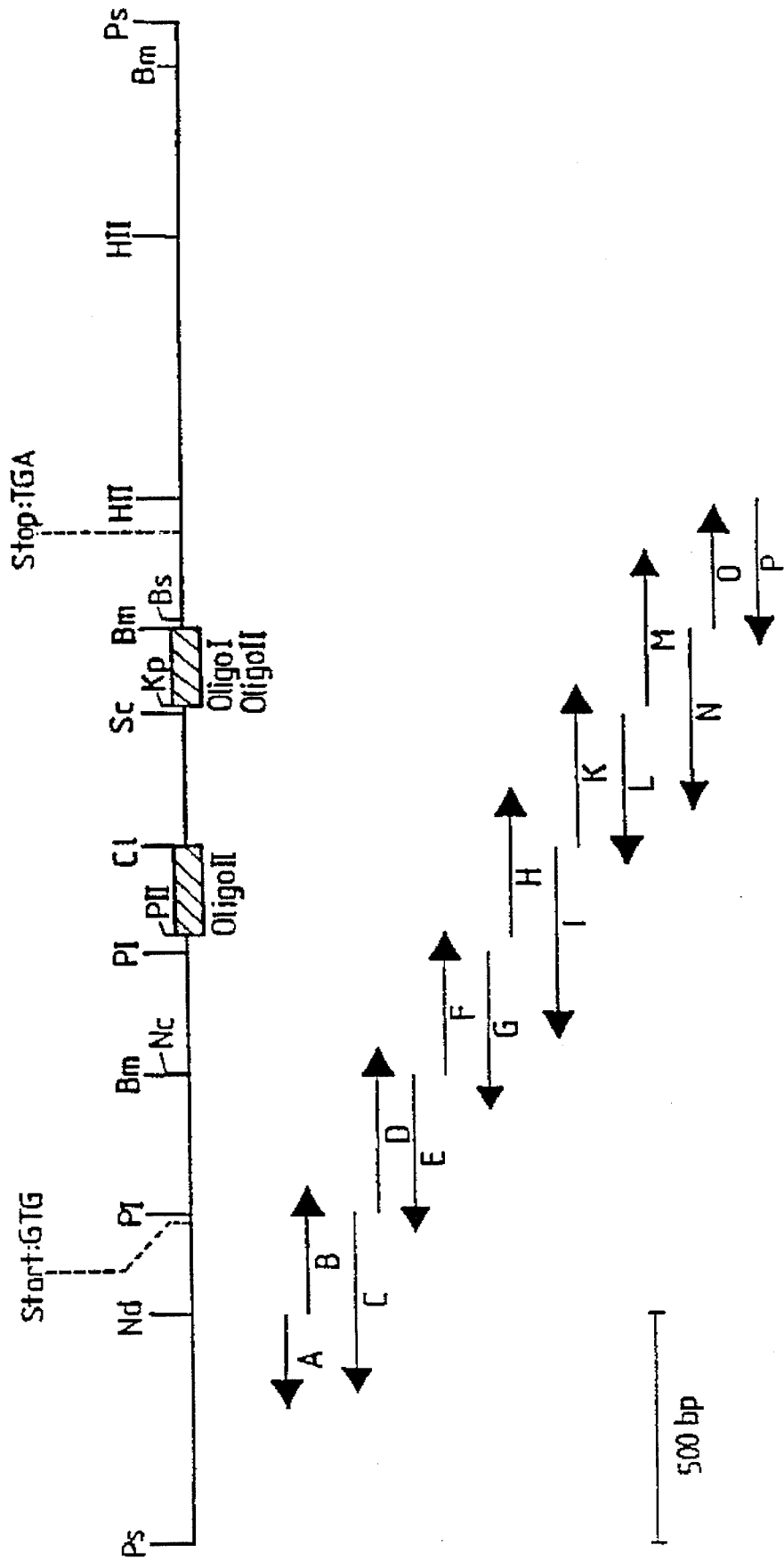

FIG. 6 shows the restriction map of the cloned 3.3 kb PstI restriction fragment which arises from the exact position of the carbamate hydrolase gene (Start: GTG=Start codon, Stop: TGA=Stop codon).

The sequenced areas are characterised by arrows under the restriction map. From the length of the arrow can be read the length of the individual sequenced areas.

The restriction fragments which contain the homology areas of the oligonucleotides described in Example 4 are emphasised in the map. (-■-).

The M13 clones are described as follows:

| Clone | Inserted Fragment | | M13 Vector |
|---|---|---|---|
| A | NdeI/SacI (pUC19) | ~500 | mp 18 |
| B | NdeI/SacI | 1289 bp | mp 18 |
| C | PvuI/PstI | ~700 bp | mp 19 |
| D | PvuI/PvuI | 564 bp | mp 18 |
| E | BamHI/BamHI (pUC 19) | | mp 18 |
| | | ~1060 bp | |
| F | BamHI/BamHI | 958 bp | mp 18 |
| G | PvuI/PvuI | 564 bp | mp 18 |
| H | PvuII/SacI | 476 bp | mp 18 |
| I | ClaI/BamHI | 561 bp | mp 18 |
| K | ClaI/BamHI | 397 bp | mp 18 |
| L | PvuII/SacI | 476 bp | mp 19 |
| M | KpnI/HindII | 445 bp | mp 19 |
| N | BamHI/BamHI | 958 bp | mp 18 |
| O | BamHI/BamHI | 1100 bp | mp 18 |
| P | KpnI/HindII | 445 bp | mp 18 |

FIGS. 7, 7A and 7B (SEQ ID NO: 6) shows the nucleotide sequence of the carbamate hydrolase gene including the 5' and 3' flanking area.

Particularly characterised are:
1. The GTG start codon
2. The ribosomal binding site (Shine-/Dalgarno Bos: S/D)
3. The homology area of the oligonucleotide described in Example 4 (oligo I and II/oligo III).

The coding nucleotide sequence was formally translated as an amino acid sequence. The reading frame is determined clearly by the protein level of the established amino acid partial sequences.

Figure 8:
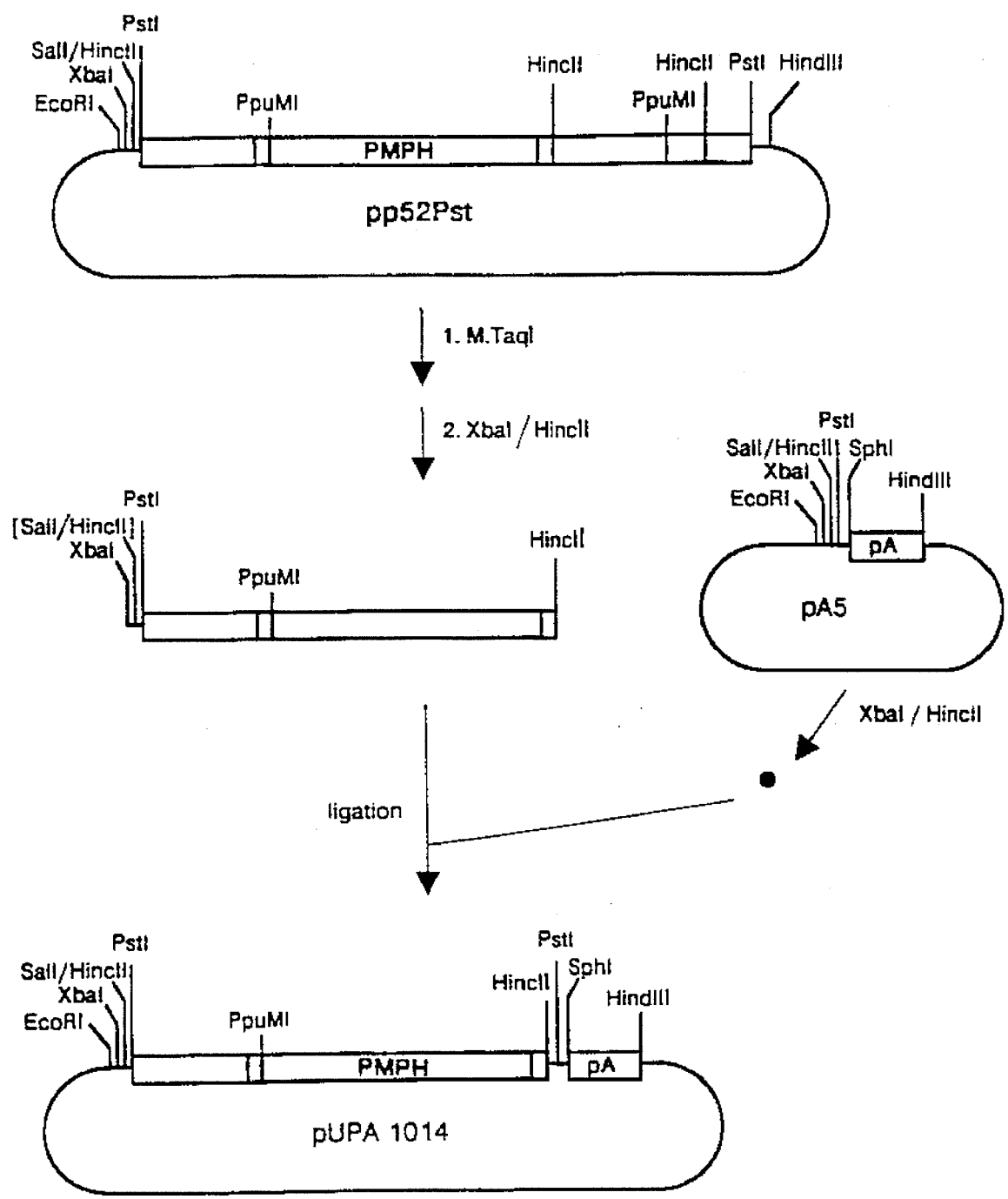

FIG. 8 shows the construction of plasmid pUPA1014. Starting from a 3.3 kb PstI fragment that originates from plasmid pHP52 (example 7) and contains the complete bacterial gene for phenmedipham carbamate hydrolase (PMPH), the untranslated 3'-region of the fragment is replaced by 0.2 kb fragment from the *Agrobacterium tumefaciens* T-DNA containing the octopine synthase gene (OCS) polyadenylation signal (pA). The vectors used are pUC19 (for pp52Pst) and pUC18 (for pA5 and pUPA1014).

Figure 9:
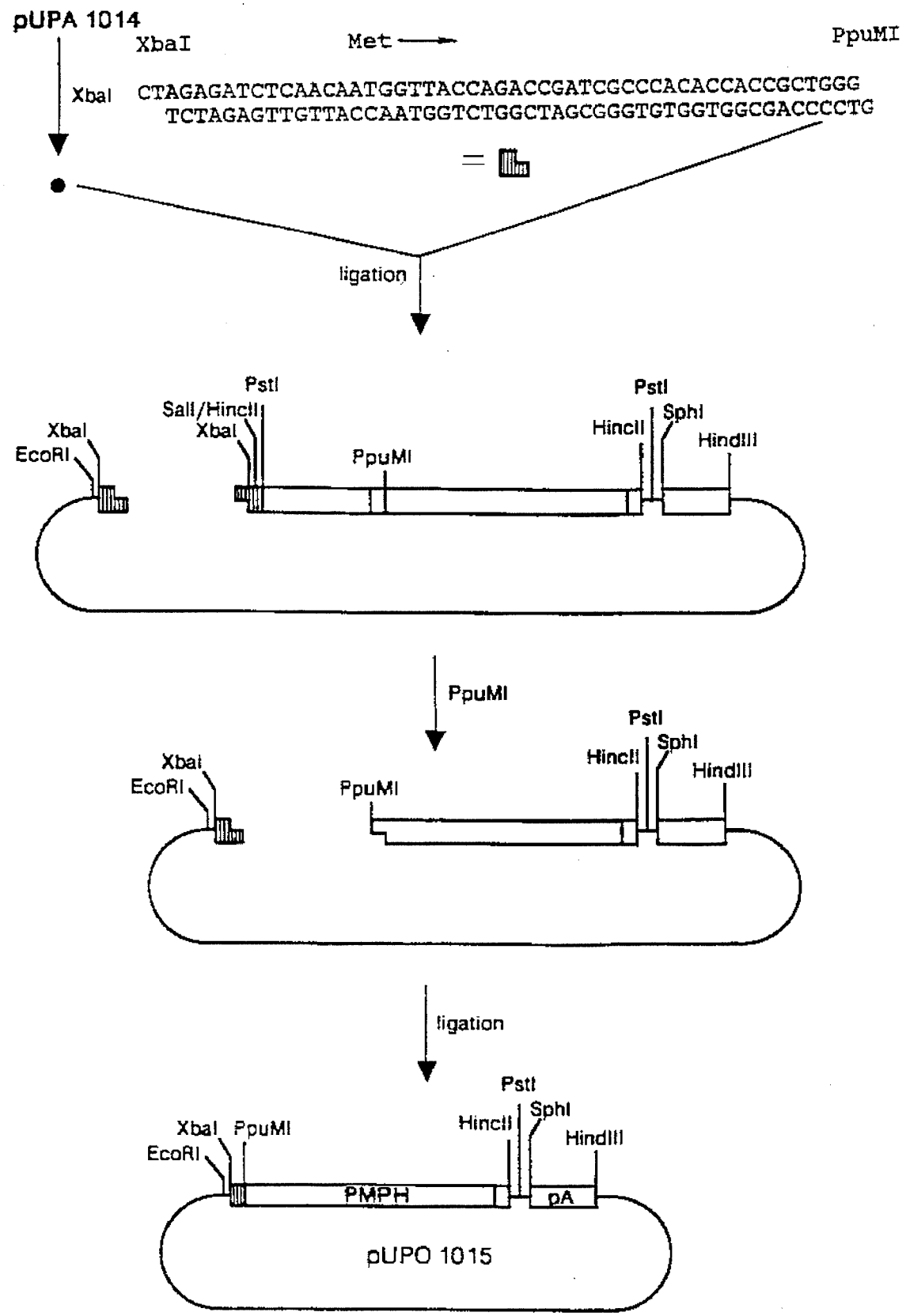

FIG. 9 shows the construction of plasmid pUPO1015. In this cloning step the untranslated 5'-region and the N-terminal part of the coding region is removed from the carbamate hydrolase gene and replaced by a synthetic double-stranded oligonucleotide, which reconstitutes the sequence coding for the N-terminal part of the protein. The sequence surrounding the translational start codon is optimal for plant gene expression according to Lütcke et al. EMBO J. 6:43–48, 1987.

Figure 10:
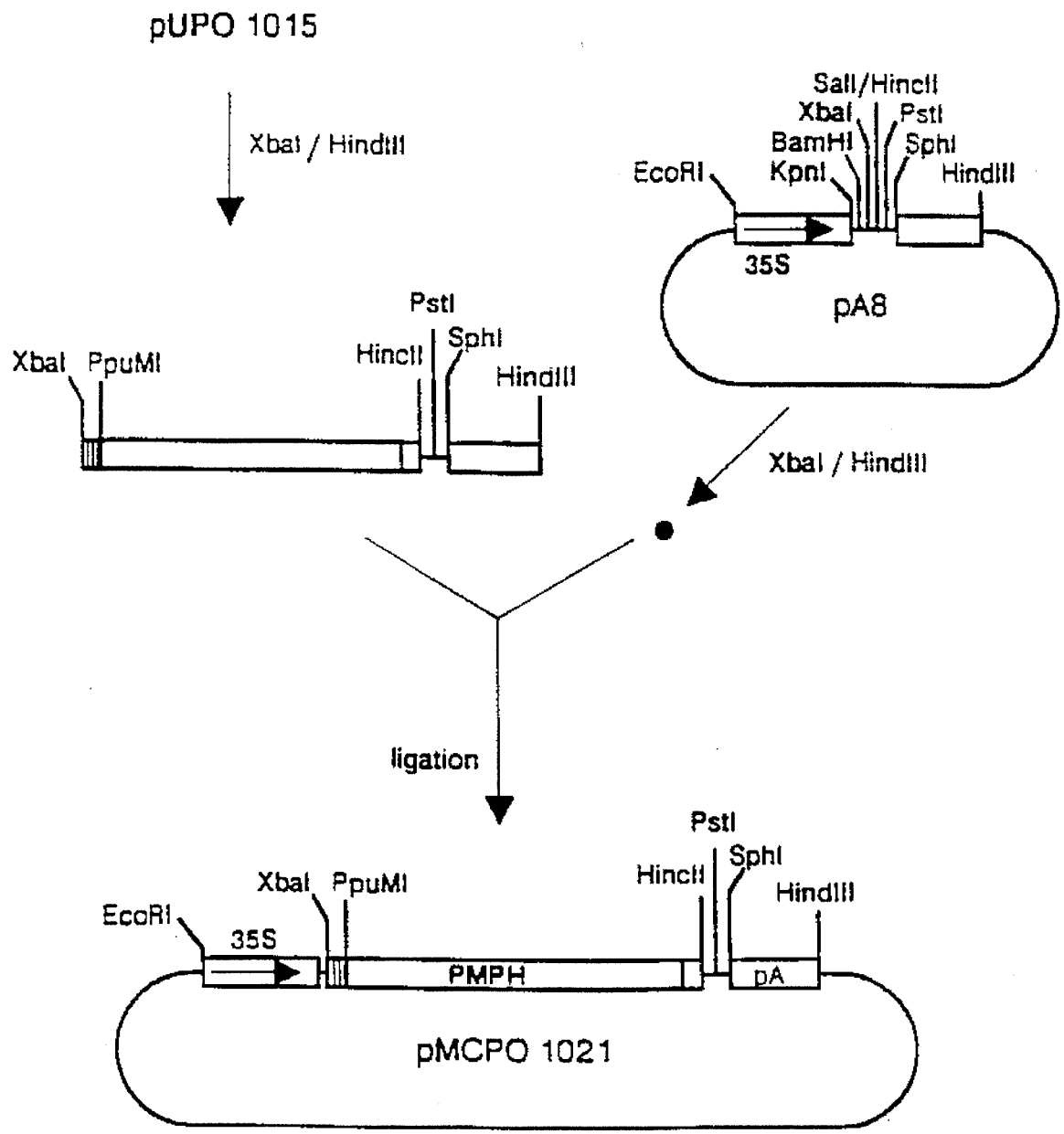

FIG. 10 shows the construction of plasmid pMCPO1021. In this cloning step, the coding sequence of the recombinant carbamate hydrolase gene is linked at its 5'-end to the cauliflower mosaic virus (CaMV) 35S promoter contained in plasmid pA8.

Figure 11:
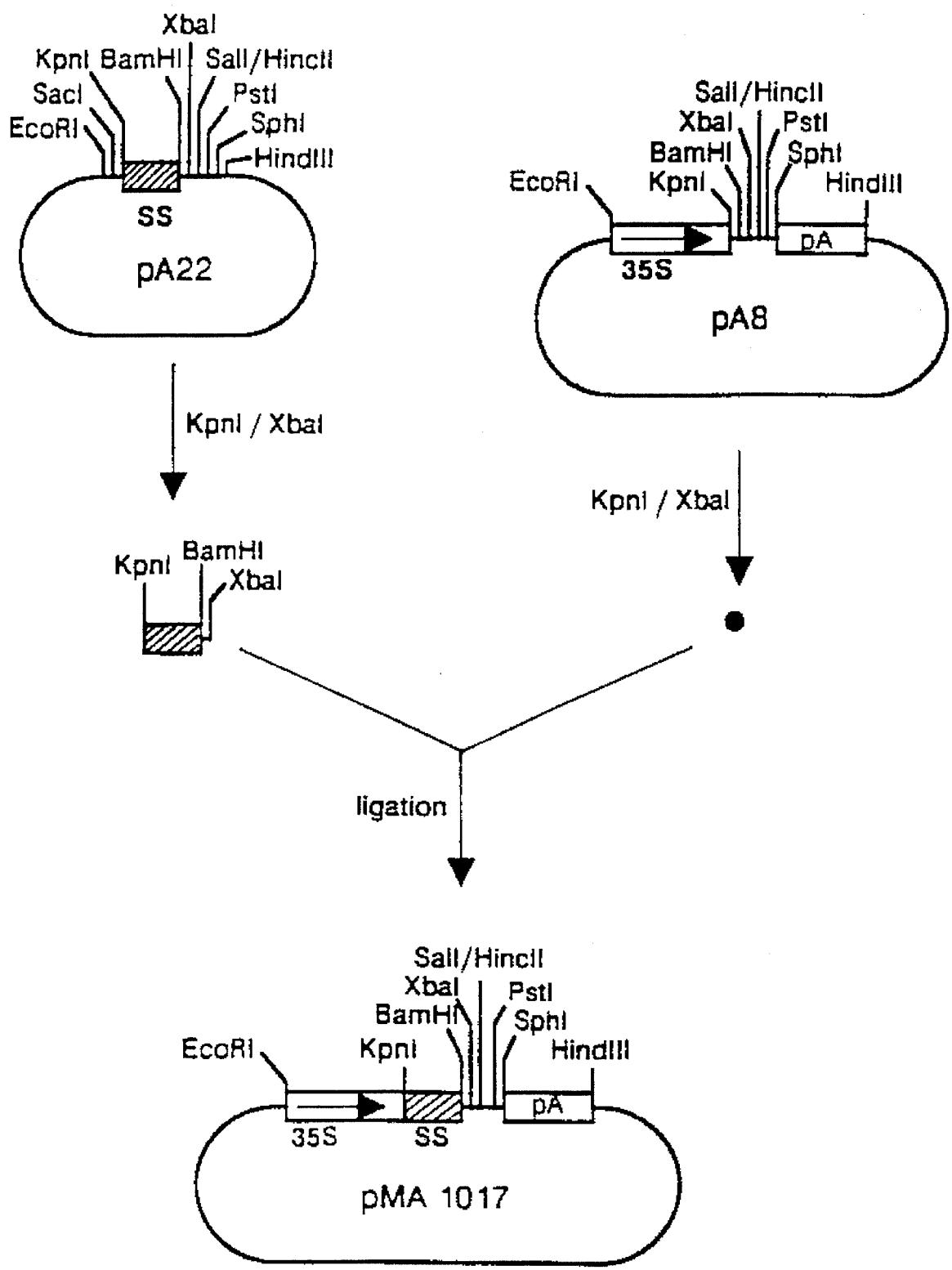

FIG. 11 shows the construction of plasmid pMA1017. In this cloning step a fragment containing the sequence hat codes for the potato proteinase inhibitor II signal peptide is inserted in correct orientation between the CaMV 35S promoter and the OCS polyadenylation signal of plasmid pA8 to create an expression vector for targeting introduced genes into the endoplasmatic reticulum of plant cells.

Figure 12:
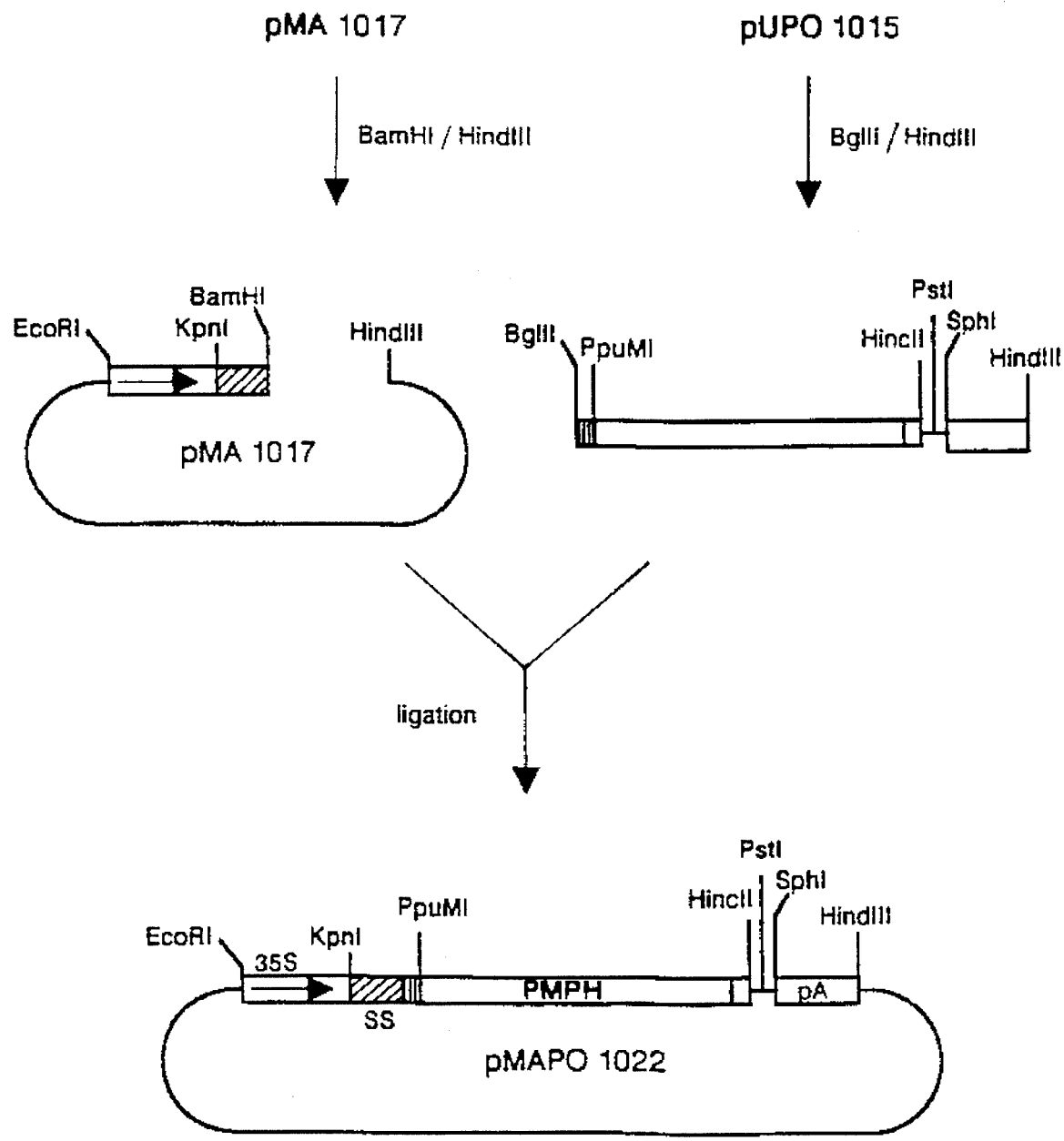

FIG. 12 shows the construction of plasmid pMAPO1022. In this cloning step the coding sequence of the recombinant carbamate hydrolase gene is linked at its 5'-end in the correct reading frame to the signal peptide sequence contained in plasmid pMA1017.

Figure 13A:
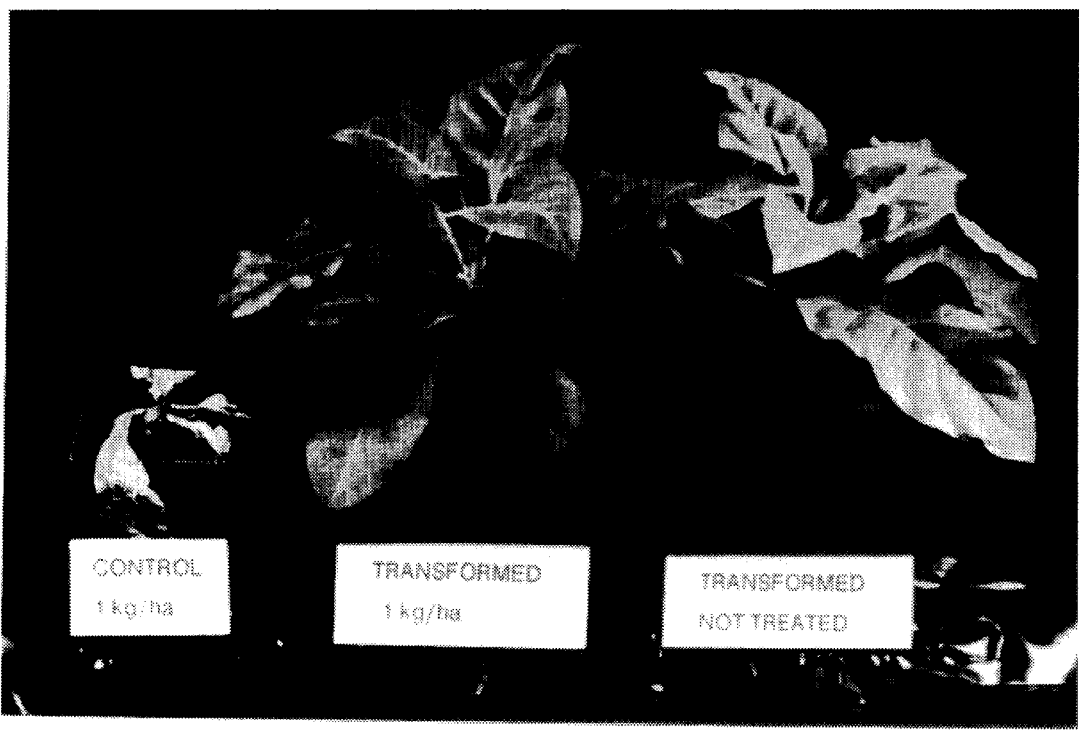
Figure 13B:
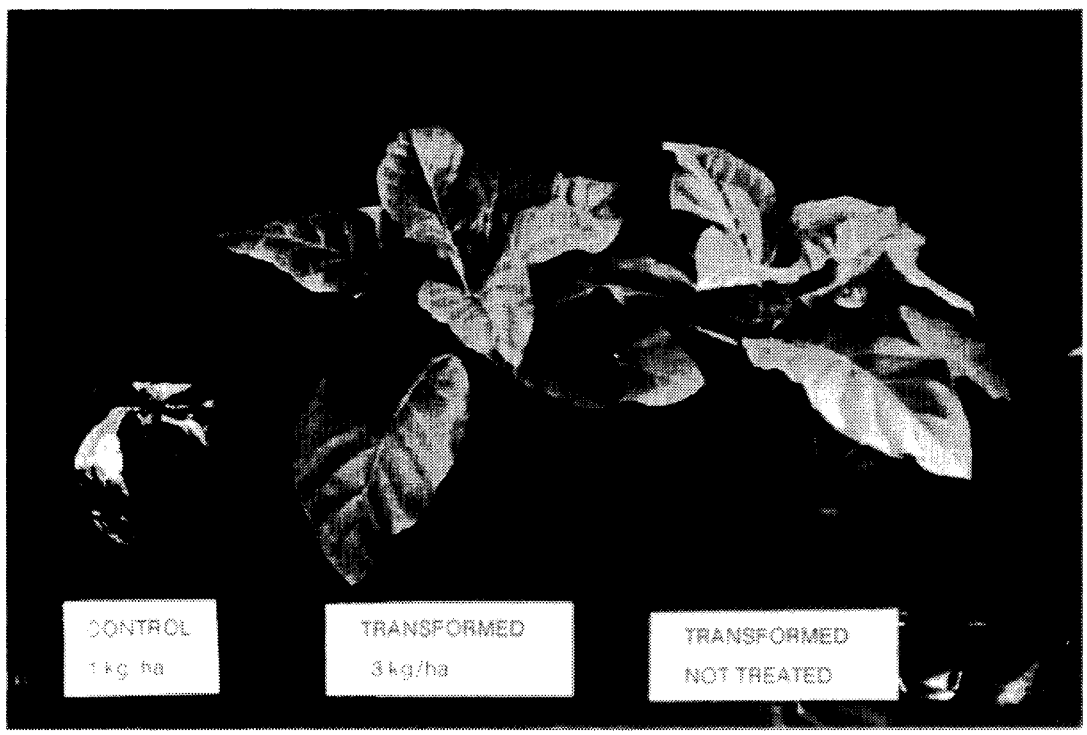
Figure 13C:
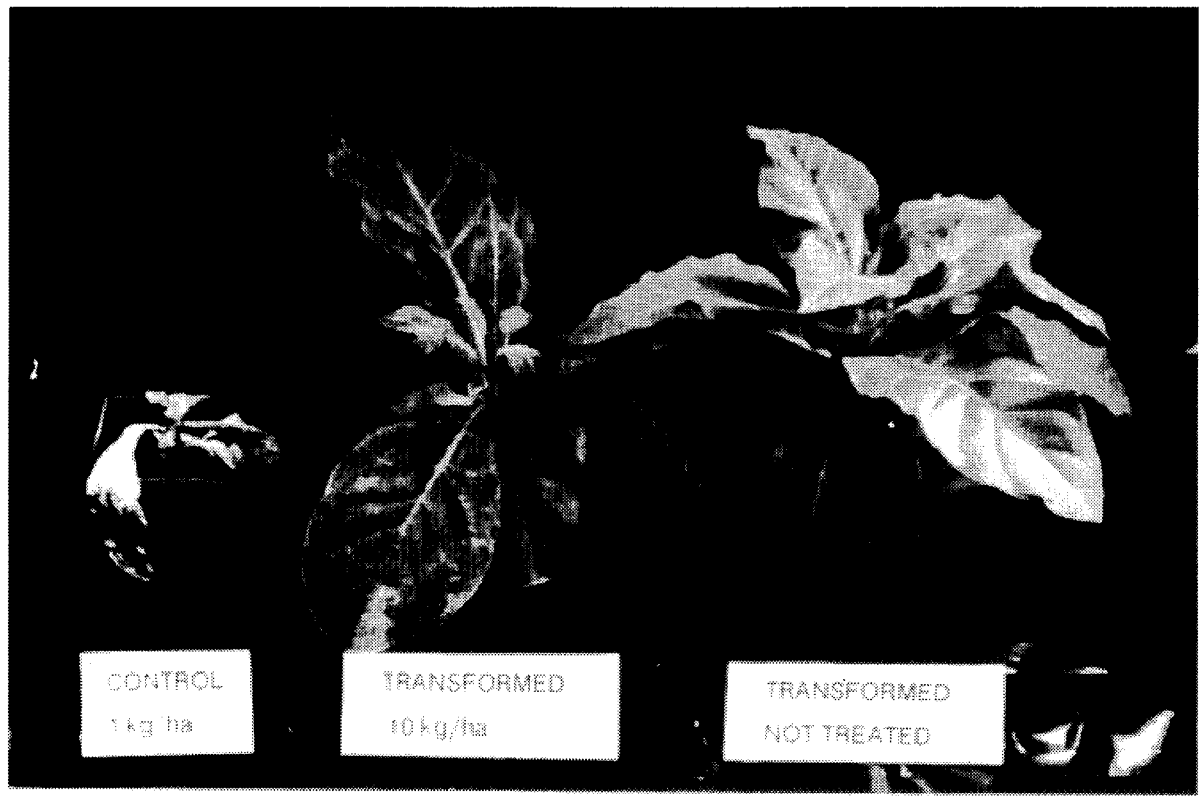

FIG. 13 shows transgenic tobacco plants WS28-19 in comparison with untransformed control tobacco W38 three weeks after treatment with the herbicide phenmedipham. FIG. 13A shows a control plant (left) which was sprayed with 1 kg/ha phenmedipham, a transformed plant (middle) which was sprayed with 1 kg/ha of phenmedipham and a transformed plant (right) which was not treated. FIG. 13B shows a control plant (left) which was sprayed with 1 kg/ha phenmedipham, a transformed plant (middle) which was sprayed with 3 kg/ha and a transformed plant (right) which was not treated. FIG. 13C shows a control plant (left) which was sprayed with 1 kg/ha phenmedipham, a transformed plant (middle) which was sprayed with 10 kg/ha and a transformed plant (right) which was not treated.

Figure 14:
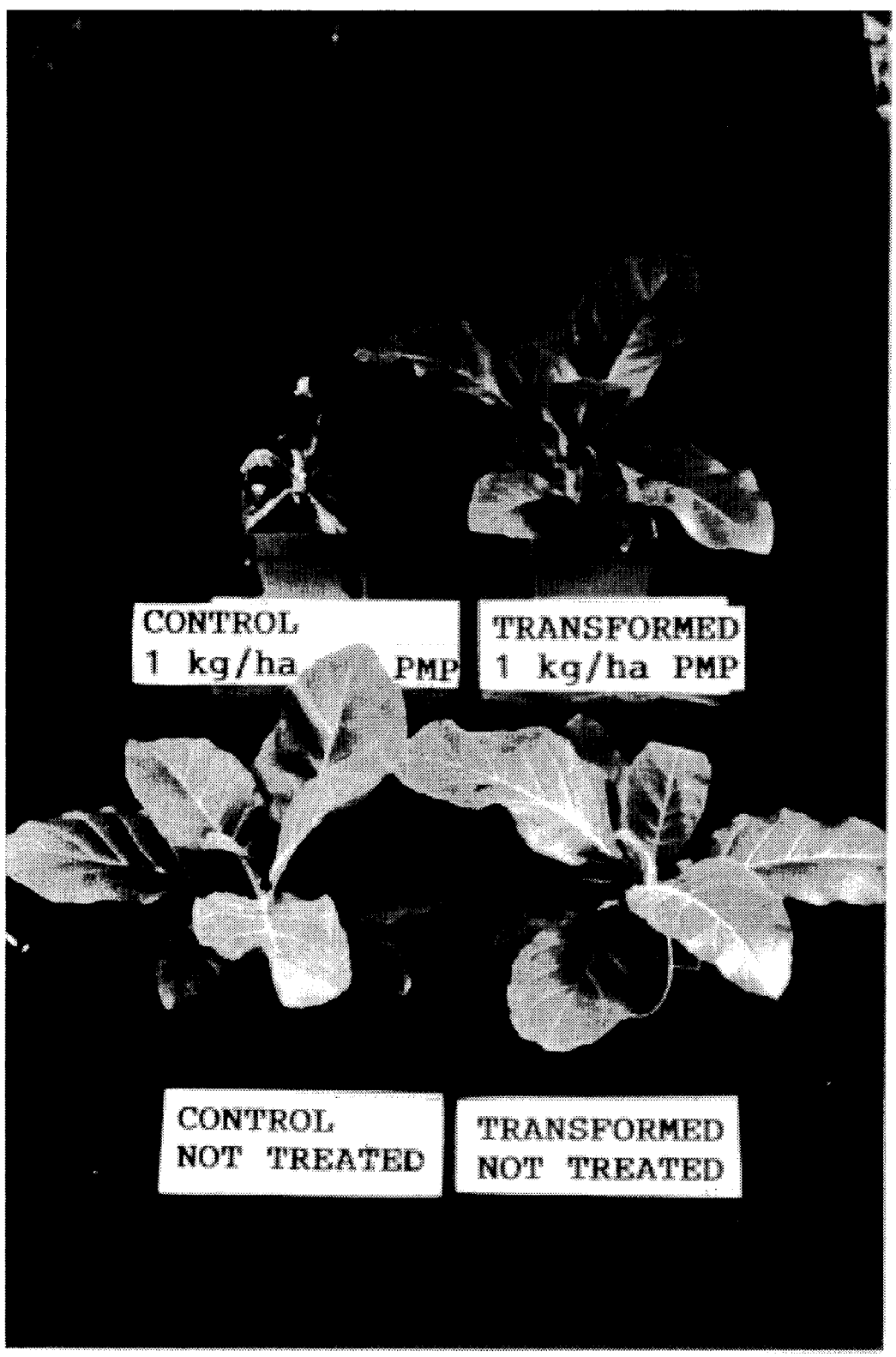

FIG. 14 shows transgenic tobacco plants WS28-19 in comparison with untransformed control tobacco W38 three weeks after treatment with the herbicide phenmedipham. FIG. 14 shows an untransformed control plant (left) and transformed plants (right) which were treated with 1 kg/ha phenmedipham (upper row), or left untreated (lower row), respectively.

Figure 15:
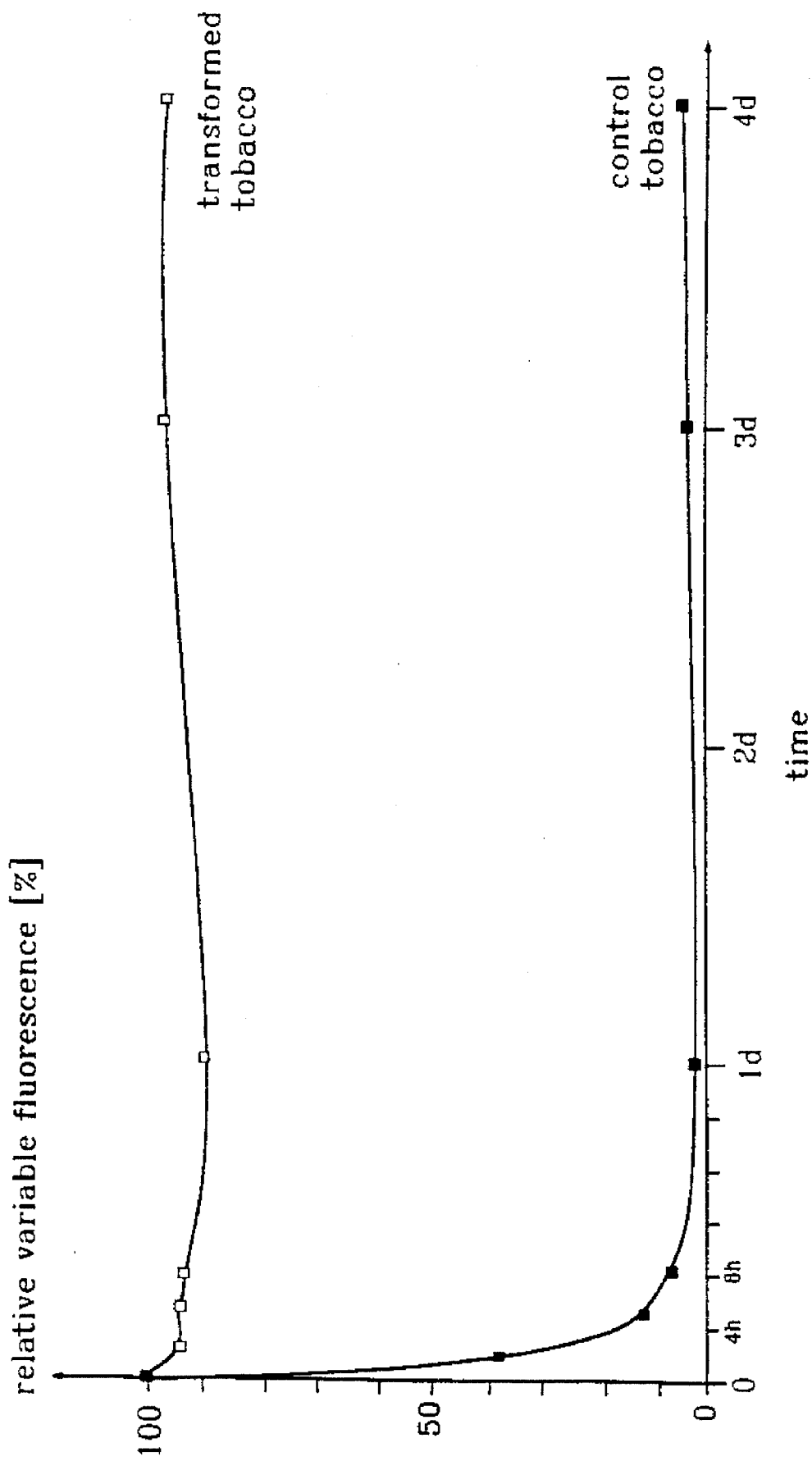

FIG. 15 shows the relative variable fluorescence of intact leaves from a control W38 plant and a transgenic plant WS28-19 after treatment with 1 kg/ha phenmedipham. Measurements were made at indicated intervals after spraying (t=0) as described in the text. Between measurements plants were further incubated in the growth chamber under 16 hours light and 8 hours dark.

EXAMPLE 1

Isolation of microorganisms that possess the ability to inactive the herbicide phenmedipham.

To identify microorganisms which possessed the ability to inactivate the herbicide phenmedipham by metabolism, various microorganisms were screened. As source for the microorganisms, soil samples from various locations (filed test sites which had been treated several times with phenmedipham), and also from settling sediment, were used. Selection criteria for the identification of microorganisms which can carry out a carbamate cleavage, were as follows.

a) Growth in a nutrient medium with phenmedipham as a single carbon or nitrogen source.

b) Breaking down of phenmedipham to highly water soluble compounds according to the following reaction.

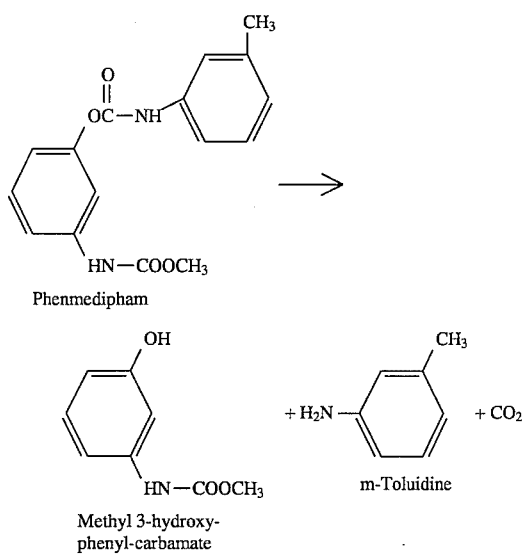

Phenmedipham

Methyl 3-hydroxy-phenyl-carbamate m-Toluidine

From the large number of microorganisms obtained from the soil samples, which were capable of cleavage of phenmedipham, seven representatives were chosen which clearly showed a breakdown. These soil bacteria which are all representatives of the Arthrobacter species and within this species, the sub-species of oxidane, were cultivated in culture broths containing a synthetic medium (M9-medium) having the following composition:

1.0 g/l $NH_4Cl$
0.25 g/l $MgSO_4 \cdot 7H_2O$
3.0 g/l $KH_2PO_4$
7.0 g/l $Na_2HPO_4 \cdot 2H_2O$
2.0 g/l Glucose and
0.5 g/l NaCl.

The M-9-medium, in addition, contained 1 mg/l thiamine (vitamin B1) as well as trace elements which were added in the form of a stock solution (1 ml/l M9-medium). The trace element stock solution contained:

0.5 Boric acid
0.04 g/l $CuSO_4 \cdot 5H_2O$
0.2 g/l $FeCl_3 \cdot 6H_2O$
0.4 g/l $MnSO_4 \cdot 7H_2O$
0.4 g/l $ZnCl_2$
0.2 g/l $(NH_4)_6Mo_7O_{24} \cdot 4H_2O$ For shaking cultures in liquid mediums, the synthetic medium was supplemented by 0.1% casamino acids (Difco[R]).

The soil bacteria were incubated in this M9 medium at 28° C. with good aeration until the end of the logarithmic growth phase. For enzyme purification, a total of 10 liters of medium were inoculated with a stationary pre-culture (1:100).

By HPLC analysis of the culture broth it was shown that in the cultures of *Arthrobacter oxidans*, the desired cleavage of phenmedipham to the herbicidally inactive products was achieved.

EXAMPLE 2

Isolation and purification of the carbamate hydrolase from *Arthrobacter oxidans*.

The isolation and subsequent purification of the carbamate hydrolase to electrophoretic homogeneity was carried out over a six stage purification process. From 6 liters of an end logarithmic culture of *Arthrobacter oxidans* (pHP52) (DSM No 4044), 0.5–1 mg carbamate hydrolase was reproducibly isolated. For isolation of the carbamate hydrolase, the cells were harvested by centrifugation (7000×g) and resuspended in about 40 ml of decomposition buffer (10 mM sodium phosphate pH 6.8 /1 mM DTT). The cell suspension was disrupted by ultrasound and homogenised at the same time. The homogenate was then centrifuged for 45 minutes at 40000×g, at 4° C. The sediment was removed and the supernatant, equilibrated with 100 mM Tris-HCl pH 7.2/100 mM NaCl/1 mM DTT, was applied to a DEAE Sephacel column (column diameter 2.6 mm, height of the gel bed 20.5 cm. column volume about 100 ml). Before application to the column, the cell extract was diluted at a ratio of about 1:10 with starting buffer (100 mM Tris/100 mM NaCl/1 mM DTT). The column was then washed with starting buffer in order to remove the unbound material. The carbamate hydrolase was then eluted with a linear gradient 100 mM NaCl—500 mM NaCl (5×column volume). The enzymatically active fractions were pooled and treated with dry ammonium sulphate $(NH_4)_2SO_4$ to an end concentration of 33% of the saturated solution. The resulting protein precipitate was sedimented by centrifugation (20000×g/30 mins) and discarded. The supernatant was treated with solid ammonium sulphate to an end concentration of 60% of the saturated solution and stirred for about 12 hours at 0° C. The sedimented protein was collected by centrifugation (20000× g/30 mins) and dissolved in about 1 ml starting buffer, treated with 10% (w/v) saccharose and loaded to a Sephacryl S-300 column. The gel filtration was carried out at a flow rate of 2.5 cm/h (elution buffer—: start buffer). The column had a diameter of 2.6 cm, a height of 95 cm and a volume of 475 ml. The enzymatically active fraction was then worked up on an FPLC column (mono Q HR 5/5: anion exchange). Gradient elution 100 mM NaCl—: 300 mM NaCl: flow rate: 0.5 ml/mm; application volume 2 ml). The unbound protein was separated by isocratic elution with 19 ml starting buffer. (Gradient elution 100 mM NaCl—: 300 mM NaCl in 20 ml with 100 mM Tris/HCl pH 7.2/1 mM DTT).

The enzymatically active fractions were concentrated by ultra-filtration after electrophoretic analysis of the purity (SDS-polyacrylamide-gel electrophoresis by the method of Lammli, using an Amicon$^{(R)}$, Centrikon 10 concentrator, and put on a FPLC gel-filtration column (Superose 6-HR 10/30, Pharmacia) (flow rate 0.2 ml/min; application volume 100 ul; eluent: 100 mM Tris/HCl pH 7.2/10 mM NaCl).

The active protein fractions which result from this step are electrophoretically homogenous.

The isolated enzyme is active in buffered solutions (ie buffers conventionally used in biochemical systems, such as phosphate buffers. Tris buffers etc: pH 6.8). Co-factors or metal ions are not necessary for the reaction. A sensitivity against SH reagents is also not seen. The optimum pH of the enzyme is 6.8.

The molecular weight of the carbamate hydrolase is in the range of 50–60, preferable 53–57 kd, both under denaturing/ dissociating conditions (SDS gel electrophoresis) as well as under native conditions (gel-filtration). From this it follows that the carbamate hydrolase is a monomeric protein. The isoelectric point of the carbamate hydrolase is at pI=6.2.

EXAMPLE 3

Process for detecting the carbamate hydrolase.

For a quick and sure determination of enzyme activity during the purification of the crude protein extracts, an in vitro enzyme test was developed. The test is based on the ability of the enzyme to change the highly water insoluble phenmedipham into a soluble hydrolysis product. For this, solid phenmedipham was suspended in water and micronised by ultrasound. This micro-suspension was then poured, with stirring at 50° C., into an agarose solution and this mixture put into a petri dish before it solidified, where it formed into a turbid gel matrix. The enzyme solution was then put into wells which had been punched in the solid matrix. After incubation of the test plates for 2–4 hours at 30° C., the enzyme activity was demonstrated by observing clear zones in the matrix which had been made opaque by the phenmedipham.

EXAMPLE 4

Identification of the amino acid sequence of two BrCN cleaving peptides and synthesis of oligonucleotides for specific evidence of the carbamate hydrolase gene by hybridization.

Resulting from the purified carbamate hydrolase, two peptides were isolated after BrCN cleavage, whose partial sequence was established by Edman degradation.

BrCN Peptide I (SEQ ID NO: 1):

$H_2N$—Ser—Asp—Glu—Phe—Ala—Asn—Leu—Asp— Arg—Trp—Thr—Gly—Lys—Pro—Phe—Val—Asp (Val)—Gly (His)—Leu—Asp—Glu—Val—Ala—Val— COOH

BrCN Peptide II (SEQ ID NO: 2):

$N_2H$—Glu—His—Thr—Lys—Phe(Val)—Asn(Gly)— Glu—Arg)Cys)—Pro—Leu—Ala—Phe—Tyr—Pro— Val—Phe—Asn—Glu—COOH

According to the amino acid sequence information of these peptides, oligonucleotides were synthesised which could be used as hybridization probes for the detection of the carbamate hydrolase gene:

Oligonucleotide I (SEQ ID NO: 3) (17 mer "mixed probe") contains as the single strand DNA fragment, the sequence information of the BrCN peptide I amino acid position 10–15 (complementary strand).

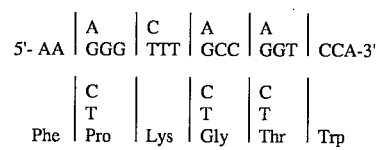

Oligonucleotide II (SEQ ID NO: 4) (42 mer) contains as a single strand DNA fragment, the sequence information of the BrCN peptide I amino acid position 8–21 (complementary strand). The codon selection was carried out under the assumption of a guanine(G) and cytosine(C) rich DNA sequence (this takes into consideration guanine(G) and cytosine(C) nucleotides before adenine(A) and thiamine(T) nucleotides on the third position of the triplets).

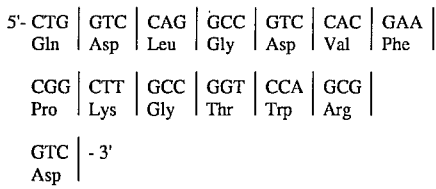

Oligonucleotide III (SEQ ID NO: 5) contains as the single strand DNA fragment sequence, information of the BrCN peptide II (complementary strand).

By using these oligonucleotides it was possible to localise the carbamate hydrolase gene within the plasmid pHP52 by hybridization. For this, the plasmid DNA was cleaved with restriction endonucleases and the resulting fragments were separated by agarose gel electrophoresis and then transferred according to the method of E. M. Southern (J. Mol. Biol. 98, 503–517 (1975)) in single strand form on membrane filters (Gene Screen Plus ™ hybridising membrane. Du Pont de Nemours/NEW Research Products).

The oligonucleotides were and end marked by use of T4-polynucleotide kinase (Boehringer Mannheim) and [γ-$^{32}$P]-adenosine-5'-triphosphate (>5000 Ci/mmol, Du Pont de Nemours/NEN Research Products) using the method of R. B. Wallace and C. G. Miyada, Methods in Enzymology 152, 432–442 (1987) and treated without further purification for the hybridisation.

The hybridization was carried out using standard processes (P. J. Mason & J. G. Williams in "Nucleic Acid Hybridisation" p. 113–160 (1985) B. D. Hames & S. J. Higgins Hrsg. IRL Press Oxform, Washington D.C.). Under the conditions 6×SSC, 10×Denhardt, 0.5% w/v SDS and 100 u/ml t RNA (B±ckerhefe, Boehringer Mannheim), as well as 10 ng/ml marked oligonucleotides I/II/III at 41° C. (=6 hours), a specific hybridisation can be achieved. The detection of the hybrids was carried out by autoradiography (T Maniatis, E G Fritsch & J Sambrook, "Molecular Cloning", Cold Spring Harbor Laboratory (1982)).

EXAMPLE 5

Isolation and characterisation of the plasmid pHP52 from *Arthrobacter oxidans* P52.

For isolation of plasmid pH52 from Arthrobacter, the alkali extraction method of Birnboim and Doly (Birnboim H. C. & Doly J. (1979) Nucl Acid Res., 7, 1513–1523) was used, with a modification by Brandsch and Decker (Brandsch, R. & Decker, K. (1984) Arch. Microbiol. 138, 15–17). For plasmid preparation, the bacteria were cultivated in 6 of LB-medium comprising:

| | |
|---|---|
| Bacto-trypton (Difco$^R$) | 10 g/l |
| Bacto-Yeast-Extract (Difco$^R$) | 5 g/l |
| NaCl | 10 g/l | to a cell density of $OD_{550}=1.4$ and harvested by centrifuging.

The cells were resuspended in a total of 210 ml solution I (50 mM gluocose: 10 mM EDTA: 25 mM Tris/HCl, pH 8.0; 1 mg/ml lysosyme) and incubated for 1 hour at room temperature. Lysis was carried out by addition of 360 ml solution II (0.2M NaOH: 1% SDS). After gentle but thorough mixing and subsequent incubation for 5 minutes at room temperature, followed by cooling on ice for 5 minutes, the mixture was neutralised the addition of 180 ml solution III (2M Tris/HCl, pH 7.0/0.5M KCl. After incubation for 1 hour on ice, the undissolved precipitate was separated by centrifugation. The plasmid DNA was precipitated from the clear supernatant by addition of 0.6 volumes isopropanol and, after an incubation of 15 minutes at room temperature, pelleted by centrifugation (15,000×g/30 minutes). The plasmid-containing precipitate was dried in vacuo and dissolved in 24 ml 10×TE buffer (100 mM Tris/HCl, pH 8.0; 10 mM EDTA). This plasmid containing solution was then purified by isopycnic cesium chloride density gradient, centrifuging in the presence of Ethidium bromide (Maniatis T., Fritsch E. F. & Sambrook J. in "Molecular Cloning" (1982), Cold Spring Harbor N.Y.).

Purified plasmid DNA was mapped by restriction analysis which cut the plasmid once or gave several fragments. These fragments were resolved by agarose gel electrophoresis (0.8% w/v). Molecular weight standards used in mapping plasmid DNA were Hind III or Hind III and EcoRI digested bacteriophage DNA.

The restriction analysis data were consistent with a circular map of pHP52 (FIG. 4). The size of the plasmid is the sum of individual restriction fragments.

All the processes were carried out in this Example according to standard methods (cf. Maniatis T., Fritsch E. F. & Sambrook J. in "Molecular Cloning" Cold Spring Harbor, N.Y. (1982)).

EXAMPLE 6

Identification of the coding region of the carbamate hydrolase gene by oligonucleotide hybridisation.

By hybridisation of the restriction fragments of the plasmid pHP52 separated by gel electrophoresis and transferred on membrane filters with the $^{32}$P marked oligonucleotide described in Example 4, the position of the coding region of the carbamate hydrolase gene can be definitely correlated on the restriction map of the plasmide pHP52. In FIG. 5, the hybridizing area is enlarged. All three oligonucleotides hybridize with the central part of a PstI restriction fragment of size 3.3 kb. In FIG. 6, a detailed restriction map of the fragment is shown from which the exact positions of the hybridising areas can be seen.

EXAMPLE 7

Cloning of the carbamate hydrolase gene is E. coli and demonstration of the genes' expression under lac promoter control.

For cloning the carbamate hydrolase gene in E. coli the vector pUC19 (Yanish-Perron, C., Vieira, J. & Messing, J. (1985) Gene 13, 103ff) was used. The pUC19 DNA was linearised by cleavage with restriction nuclease PstI and treated with alkaline phosphatase. The DNA of the 3.3 kb long PstI restriction fragment of the plasmid pHP52 was isolated (after digesting the wild-type plasmid DNA with PstI) by preparative agarose gel electrophoresis. The linearised and dephosphorylated vector DNA and the 3.3 kb long PstI fragment was then ligated with T4 DNA ligase. *E. coli* DH5α was transformed with the ligation mixture.

Two types of clones were obtained which contained the fragment in different orientations to the transcription direction of the lac Z' gene of the vector pUC 19. These are the clones pp52 Pst and pp52 Pst inv. The restriction map of both clones is shown in FIG. 5. The clones of type *E. coli* pp52 Pst express carbamate hydrolase. After addition of the inductor isopropyl-β-D-thiogalactopyranoside to the culture medium. Without inducer addition (repressed state of the lac promoter) to logarithmic cultures of the clone pp52 Pst as well as by repressed and induced logarithmic cultures of the clone pp52 Pst inv in enzyme extracts, no enzyme activity was seen using the assays described in Example 3.

This means that the carbamate hydrolase gene in clones of type pp52 Pst lies in the same transcription direction (5'-3' orientation) as the lac Z' gene of the vector. The Arthrobacter promoter is not or only slightly expressed in *E. coli*.

EXAMPLE 8

Nucleotide sequence of the carbamate hydrolase gene from the *Arthrobacter oxidans (species P52)* and the deduced protein sequence.

The nucleotide sequence of the carbamate hydrolase gene was established by the method of Sanger (Sanger F., Nicklen S. & Coulson A. (1977) Proc. Natl. Acad. Sci. USA, 74, 5463–5468).

For this, 15 sub-clones in the single stranded DNA bacteriophage M13 mp18 and M13 mp19 from the pp52 PST DNA were constructed (Messing, J. (1983) Methods in Enzymol. 101, 20–78). After transfection of *E. coli* DH5αF', the sequence of the single stranded recombinant DNA was established.

In FIG. 6, the sequencing strategy of the carbamate hydrolase gene is shown. Altogether the sequence of 1864 base pairs was established.

In FIGS. 7, 7A and 7B (SEQ ID NO: 6), the established nucleotide sequence is shown with the deduced amino acid sequence of the carbamate hydrolase. The reading frame is clearly defined as described by the amino acid sequences of two BrCN cleavage peptides as described in Example 4. The reading frame finishes with a TGA stop codon (nucleotide position 1789–1791 in FIGS. 7, 7A and 7B) (SEQ ID NO: 6). As a translation start codon, a GTG (nucleotide position 310–312) is suitable. This gives the longest open reading frame of 1479 bp (=493 amino acids). All open reading frame which begin with the usual ATG start codons give no protein of suitable size (compared to the molecular weight determination of the protein).

The hypothesis that translation starts from GTG (position 310–312) is further supported by the existence of a definite homologous region to the consensus sequence for ribosomal *E. coli* binding sites 7 bp upstream of the putative GTG start codon.

All cloning steps were carried out by standard processes (cf Maniatis, T., Fritsch, E. G. & Sambrook, J. (1982) in "Molecular Cloning", Cold Spring Harbor, N.Y.). The sequencing reactions were carried out using Sequenase[R] DNA Sequencing Kits (United States Biochemical Corporation) according to information by the producer. The separation of the marked reaction products was carried in 6% w/v polyacrylamide/urea gel (Maxam, A. M. & Gilbert, W. (1980) Methods Enzymol. 65, 497–559).

EXAMPLE 9

Construction of plasmids for the expression of carbamate hydrolase in plants.

a) Construction of intermediate vectors

Plasmid DNA from pp52 Pst (FIG. 8) is methylated using TaqI Methylase (M. TaqI) to make the single SalI restriction site inaccessible to HincII. Then the methylated plasmid is cut with both restriction enzymes XbaI and HincII to release a 2.2 kb DNA fragment containing the open reading frame for carbamate hydrolase. This fragment is purified by preparative agarose gel electrophoresis. The vector plasmid pA5 (FIG. 8) is cut with XbaI and HincII and then ligated with the purified 2.2 kb DNA fragment, thus linking the 3'-end of the carbamate hydrolase coding region to the polyadenylation signal of the octopine synthetase (OCS) gene (Dhaese et al., EMBO J. 2:419, 1983). Competent cells of *E. coli* DH5alpha are transformed with the recombined DNA and clones are selected on LB-agar containing 100 μg/ml carbenicillin. Clones containing the recombined plasmid pUPA1014 (FIG. 8) are identified by restriction analysis of isolated plasmid DNA.

Two oligonucleotides of the following sequence are synthesized by an automatic synthesizer:
1.) 5'-CTAGAGATCT CAACAATGGT TACCAGACCG ATCGCCCACA CCACCGCTGG G-3' (SEQ ID NO: 8)
2.) 5'-GTCCCCAGCG GTGGTGTGGG CGATCGGTCT GGTAACCATT GTTGAGATC-3' (SEQ ID NO: 9)

They represent complementary DNA strands which are able to reconstitute the N-terminal portion of the open reading frame of the carbamate hydrolase gene upstream (5') of the PpuMI restriction site.

Both complementary oligonucleotides are mixed, phophorylated by polynucleotide kinase and then annealed by shifting temperature from 70° C. to room temperature overnight. Plasmid DNA of pUPA1014 is digested with XbaI and then ligated with the annealed oligonucleotide. This covalently links two oligonucleotides at their XbaI-compatible ends to both ends of the linearised plasmid. The linear ligation product is purified by preparative agarose gel electrophoresis and digested with PpuMI to remove the N-terminal part of the coding region. The linear DNA is then recircularized by ligase treatment. Competent cells of *E. coli* DH5alpha are transformed with the recombined DNA and clones are selected on LB-agar containing 50 ug/ml carbenicillin. Clones containing the recombined plasmid pUP01015 (FIG. 9) are identified by restriction analysis of isolated plasmid DNA. The correct ligation of the oligonucleotide is verified by sequence analysis of purified pUP01015 DNA using the dideoxy method (Sanger et al., Proc. Natl. Acad. Sci. USA 74:5463, 1977) modified for plasmid DNA as template (Chen and Seeburg, DNA 4:165, 1985).

b) Construction of plasmids for the cytoplasmatic expression of carbamate hydrolase.

Plasmid DNA of pUP010115 is digested with both restriction enzymes XbaI and HindIII to create a DNA fragment that contains the whole recombinant coding region of the carbamate hydrolase together with the polyadenylation signal described above. The fragment is then ligated with the plant expression vector plasmid pA8 (A. v. Schaewen, Dissertation, FU Berlin, 1989; FIG. 10) which was similarily treated with XbaI and HindIII. The ligation links the gene in correct orientation to the cauliflower mosaic virus (CaMV) 35S promoter (Paszkowski et al., EMBO J. 3:2717, 1984) contained in pA8. Competent cells of *E. coli* DH5alpha are transformed with the recombined DNA and clones are selected on LB-agar containing 25 µg/ml streptomycin. Clones containing the recombined plasmid pMCPO1021 (FIG. 10) are identified by restriction analysis of isolate plasmid DNA.

Plasmid DNA of pMCPO1021 is digested with both restriction enzymes EcoRI and HindIII to create a DNA fragment that contains the CaMV 35S promoter, the carbamate hydrolase coding region and the OCS polyadenylation signal. The fragment is then ligated with a EcoRI and HindIII cleaved vector plasmid pBIN19 that is part of the binary transformation system described by Bevan, Nucl. Acids Rec. 12:8711, 1984. Competent cells of *E. coli* S17-1 (Simon et al. Bio/Technology 1:784–791, 1983) are transformed with the recombined DNA and clones are selected on LB-agar containing 50 µg/ml kanamycin. Clones containing the recombined plasmid pBCPO1027 are identified by restriction analysis of isolated plasmid DNA.

c) Construction of plasmids for the extracellular expression of carbamate hydrolase.

Plasmid pA22 (FIG. 11) contains a synthetic intronless sequence that codes for the signal peptide of the proteinase inhibitor II (PI) from potato and can be attached to the N-terminus of other genes to direct the gene product into the endoplasmatic reticulum of the plant cell. To create an intermediate vector for targeting of carbamate hydolase, the DNA fragment encoding the signal peptide is excised from plasmid pA22 by cleavage with restriction enzymes KpnI and XbaI and then ligated with a KpnI and XbaI cleaved plasmid pA8. Competent cells of *E. coli* DH5alpha are transformed with the recombined DNA and clones are selected on LB-agar containing 25 µg/ml streptomycin. Streptomycin resistant clones are then screened for the loss of plasmid pA22 on LB-agar containing 50 µg/ml carbenicillin. Carbenicillin sensitive clones are analyzed by restriction analysis of isolated plasmid DNA and recombined plasmids containing the signal peptide encoding sequence are designated pmA 1017 (FIG. 11).

Plasmid DNA of pUPO1015 id digested with both restriction enzymes HindIII and BglII to create a DNA fragment that contains the whole recombinant coding region of the carbamate hyrolase together with the polyadenylation signal described above. The fragment is then ligated with the plant expression vector plasmid pMA1017 which has been digested with BamHI and HindIII. The ligation links the gene in correct orientation to the cauliflower mosaic virus (CaMV) 35S promoter (Paszkowski et al., EMBO J. 3:2717, 1984) and the proteinase inhibitor signal sequence described above. Competent cells of *E. coli* DH5alpha are transformed with the recombined DNA and clones are selected on LB-agar containing 25 µg/ml streptomycin. Clones containing the recombined plasmid pMAP01022 (FIG. 12) are identified by restriction analysis of isolated plasmid DNA.

Plasmid DNA of pMAP010122 is digested with both restriction enzymes EcoRI and HindIII to create a DNA fragment that contains the CaMV 35S promoter, the PI signal sequence linked in frame to the carbamate hydrolase coding region and the OCS polyadenylation signal. The fragment is then ligated with a EcoRI and HindIII cleaved vector plasmid pBIN19 (Bevan, Nucl, Acids Res. 12:8711, 1984). Competent cells of *E. coli* S17-1 (Simon et al. Bio/Technology 1:784–791, 1983) are transformed with the recombined DNA and clones are selected on LB-agar containing 50 µg/ml kanamycin. Clones containing the recombined plasmid pBAP01027 are identified by restriction analysis of isolated plasmid DNA.

EXAMPLE 10

Transformation of tobacco with chimeric carbamate hydrolase genes a) Transfer of recombinant carbamate hydrolase from *E. coli* to *A. tumefaciens*

Strains of *E. coli* S17-1 containing chimeric carbamate hydrolase gene on plasmids pBCPO1027 or pBAP01028 are grown at 37° C. in liquid LB medium containing 50 µg/ml kanamycin. *Agrobacterium tumefaciens* LBA4404 (Bevan, Nucl. Acids Res. 12:8711, 1984) is grown at 28° C. in liquid YEB medium (Yeast extract 1 g/l, beef extract 5 g/l, peptone 5 g/l, sucrose 5 g/l, sucrose 5 g/l, MgSO$_4$ 0.5 g/l). 0.4 ml samples of *E. coli* culture are centrifuged and the bacterial pellets are resuspended in 0.4 ml YEB. Bacterial suspensions of *E. coli* in YEB and samples of *Agrobacterium tumefaciens* culture in YEB are then mixed in a 1:1 ratio in relation to cell density. Samples 50–100 µl from the mixtures are spotted onto LB-agar and incubated at 28° C. for 6–16 hours. Bacterial mating mixtures that have grown on the agar are suspended in liquid M9-salts (6 g/l Na$_2$HPO$_4$, 3 g/l KH$_2$PO$_4$, 0.5 g/l NaCl, 1 g/l NH$_4$Cl. 2 mM MgSO$_4$, 0.1 mM CaCl$_2$, 1 mM HCl) and then plated in several dilutions onto M9-agar containing 2 g/l sucrose and 50 µg/ml kanamycin. Plates are incubated at 28° C. for several days until bacterial colonies have grown. These colonies are further purified by subsequent cultivation on the same medium. That these clones of *A. tumefaciens* LBA4404 contain recombinant plasmids pBCPO1027 and pBAP01028 respectively is verified by restriction analysis of isolated plasmid DNA.

b) Transfer of recombinant carbamate hyrolase from *A. tumefaciens* to tobacco.

For transformation of tobacco, *A. tumefaciens* strains harbouring carbamate hydrolase plasmids are grown overnight at 28° C. in liquid YEB medium containing 50 µg/ml kanamycin. Cells are centrifuged at 5000 g for 15 minutes and resuspended in the same volume of YEB without antibiotic. *Nicotians tabacum* Wisconsin W38 plantlets are grown under sterile conditions on solid MS medium containing 20 g/l sucrose. Leaves are cut from those plants, dissected into pieces of around 1 cm$^2$ and rinsed with the bacterial suspension. Leaf disks are then placed onto solid MS medium containing 20 g/l sucrose. After 2 days of incubation at room temperature in the dark leaf disks are transferred to solid MS medium containing 16 g/l glucose, 1 mg/l benzylaminopurine, 0.2 mg/l naphthylacetic acid, 500 mg/l claforan and 50 mg/l kanamycin. Incubation is continued at 25° C. under a daily regime of 16 hours light (photosynthetically active radiation=67 µEM$^{-2}$s$^{-1}$) and 8 hours dark. The medium is changed every week until shoots appear. These are cut from the callus and transferred to MS medium containing 20 g/l sucrose and 250 mg/l claforan. Incubation is continued under the same conditions until roots of 1–2 cm in length have formed and plants are transferred to soil. Total RNA isolated from leaves is analyzed by northern blot hybridisation using the 1.8 kb EcoRI-HindIII fragment of pUPO1015 as a labeled probe. Transformed plants synthesize a transcript of around 1.8 kb in size that specifically hybridizes with the carbamate hydrolase coding sequence.

EXAMPLE 11

Detection of transformed plants which are resistant to the herbicidal activity of phenmedipham.

Transgenic plants are transferred to soil and grown in a growth chamber at 25° C. with a day/night rhythm of 16 hours light and 8 hours dark. No difference in growth can be seen between transformed and untransformed tobacco. Plants that have a leaf length of around 10 cm are sprayed with the herbicide Betanal® (active ingredient: 157 g/l phenmedipham).

Doses corresponding to field application rates of 1 kg/ha. 3 kg/ha and 10 kg/ha are used to distinguish between resistant plants and untransformed wildtype plants: Whereas 1 kg/ha is completely lethal for wildtype plants, transgenic plants which express the carbamate hydrolase gene show resistance levels between 1 kg/ha and 10 kg/ha (FIG. 13 and 14).

The same spraying experiment is done by using Betanal® AM (active ingredient: 157 g/l desmedipham) as the herbicidal agent.

EXAMPLE 12

Analysis of herbicide detoxification in plants sprayed with phenmedipham.

Transgenic tobacco plants expressing carbamate hydrolase and untransformed control plants are grown as described in example 11 and sprayed with the herbicide Betanal® corresponding to 1 kg/ha phenmedipham. Normalized variable fluorescence is measured on intact leaves of sprayed plants as is described by Voss. Weed Science 32:675–680 (1984). The equipment used is a Kompakt-Fluorometer RKF 1000 (Ingenieurburo F.U.R. Dr. M. Voss, Berlin). Measurement values before spraying are taken as 100% relative variable fluorescence. Subsequent measurements are performed in a time course of 2, 4, 8, 24 hours and then very day up to 4 days. Relative variable fluorescence values of transgenic tobacco plants expressing carbamate hydrolase stay constantly higher than 90% in contrast values from untransformed tobacco fall below 10% within the first 8 hours after spraying (FIG. 15).

The same spraying experiment is done by using Betanal® AM (active ingredient: 157 g/l desmedipham) as the herbicidal agent.

---

We claim:

1. Oligonucleotides having the nucleotide sequences:

Nucleotide I (SEQ ID NO:8):

5'-CTAGAGATCT CAACAATGGT TACCAGACCG ATCGCCCACA CCACCGCTGG G-3'

Nucleotide II (SEQ ID NO:9):

5'-GTCCCCAGCG GTGGTGTGGG CGATCGGTCT GGTAACCATT GTTGAGATC-3'.

2. A method for the reconstitution of the N-terminal portion of the open reading frame of a carbamate hydrolase gene upstream (5') of the PpuMI restriction site, wherein said method comprises the step of:

ligating oligonucleotides to said carbamate hydrolase gene, wherein the oligonucleotides comprise:

Nucleotide I (SEQ ID NO: 8):

5'-CTAGAGATCT CAACAATGGT TACCAGACCG ATCGCCCACA CCACCGCTGG G- 3' and

Nucleotide I (SEQ ID NO: 9): 5'-GTCCCCAGCG GTGGTGTGGG CGATCGGTCT GGTAACCATT GTTGAGATC-3'.

3. A purified and isolate carbamate hydrolase gene capable of inactivating phenmedipham.

4. A vector comprising oligonucleotides, wherein the oligonucleotides comprise:

Nucleotide I (SEQ ID NO: 8):

5'CTAGAGATCT CAACAATGGT TACCAGACCG ATCGCCCACA CCACCGCTGG G-3'; and

Nucleotide II (SEQ ID NO: 9):

5'-GTCCCCAGCG GTGGTGTGGG CGATCGGTCT GGTAACCATT GTTGAGATC-3'.

5. The purified and isolated carbamate hydrolase gene according to claim 3, wherein the carbamate hydrolase gene has the activity of a carbamate hydrolase from *Arthrobacter oxidans* when it is expressed.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Arthrobacter oxidans
        ( B ) STRAIN: P52

( x i ) SEQUENCE DESCRIPTION: SEQ ID NO:1:

```
Ser  Asp  Glu  Phe  Ala  Asn  Leu  Asp  Arg  Trp  Thr  Gly  Lys  Pro  Phe  Val
1                   5                        10                            15

Xaa  Xaa  Leu  Asp  Glu  Val  Ala  Val
                20
```

( 2 ) INFORMATION FOR SEQ ID NO:2:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal (vi) ORIGINAL SOURCE:
(A) ORGANISM: Arthrobacter oxidans
(B) STRAIN: P52

(xi) SEQUENCE DESCRIPTION: SEQ ID NO:2:

Glu His Thr Lys Xaa Xaa Glu Xaa Pro Leu Ala Phe Tyr Pro Val Phe
1               5                   10                  15

Asn Glu (2) INFORMATION FOR SEQ ID NO:3:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: NO (vi) ORIGINAL SOURCE:
(A) ORGANISM: Arthrobacter oxidans
(B) STRAIN: P52

(xi) SEQUENCE DESCRIPTION: SEQ ID NO:3:

AANGGYTTNC CNGTCCA                                                    17

(2) INFORMATION FOR SEQ ID NO:4:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: NO (vi) ORIGINAL SOURCE:
(A) ORGANISM: Arthrobacter oxidans
(B) STRAIN: P52

(xi) SEQUENCE DESCRIPTION: SEQ ID NO:4:

CTGGTCCAGG CCGTCCACGA ACGGCTTGCC GGTCCAGCGG TC                         42

(2) INFORMATION FOR SEQ ID NO:5:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: NO (vi) ORIGINAL SOURCE:
(A) ORGANISM: Arthrobacter oxidans
(B) STRAIN: P52

(xi) SEQUENCE DESCRIPTION: SEQ ID NO:5:

TTCGTTGAAG ACCGGGTAGA ACGC                                            24

( 2 ) INFORMATION FOR SEQ ID NO:6:

( i ) SEQUENCE CHARACTERISTICS:
        ( A ) LENGTH: 1864 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: RBS
        ( B ) LOCATION: 298..302

( i x ) FEATURE:
        ( A ) NAME/KEY: CDS
        ( B ) LOCATION: 310..1791
        ( D ) OTHER INFORMATION: /codon=(seq: "gta", aa: Val)
                      / product="carbamate hydrolase"
                      / transl_except=(pos: 310 .. 312, aa: Met)
                      / note="terminator (1789-1791)"

( i x ) FEATURE:
        ( A ) NAME/KEY: mat_peptide
        ( B ) LOCATION: 310..1788

( x i ) SEQUENCE DESCRIPTION: SEQ ID NO:6:

```
TCCTTGCCAG  TCACGGCACC  CCAGCCAACC  CGGAAGTGGC  ACCTGCTCGG  GCACATCGGT        60

GCGAACGCTT  CGTCCTGATT  CCGATGCCAA  CTGCTTGACG  GCCGTGACAC  ATATGTAGCA       120

TAGTCGCCTA  GCATGGACCC  GCAGCACACC  TGCTGTCGGC  TCCCGCGCTA  TCCCCGACCA       180

GCGCCGGTCA  CGGGTAGTCC  TCGTGAGAGG  CACCAGAACG  ACAACGGCGC  ACTGTCCCGC       240

AACACGGCCG  TATAACCCCA  CCGGGGTCCG  CGCCCGAGCT  AGTTCTGGCT  CAACCATAAG       300

GAGAACCTC  GTG  ATT  ACC  AGA  CCG  ATC  GCC  CAC  ACC  ACC  GCT  GGG  GAC                348
           Met  Ile  Thr  Arg  Pro  Ile  Ala  His  Thr  Thr  Ala  Gly  Asp
             1                  5                           10

CTC  GGC  GGT  TGC  CTT  GAA  GAC  GGC  CTG  TAC  GTG  TTC  CGA  GGA  GTG  CCG       396
Leu  Gly  Gly  Cys  Leu  Glu  Asp  Gly  Leu  Tyr  Val  Phe  Arg  Gly  Val  Pro
      15                  20                       25

TAC  GCC  GAG  CCG  CCG  GTC  GGC  GAC  CTG  CGG  TGG  CGG  GCG  GCG  CGC  CCG       444
Tyr  Ala  Glu  Pro  Pro  Val  Gly  Asp  Leu  Arg  Trp  Arg  Ala  Ala  Arg  Pro
 30                       35                       40                       45

CAC  GCC  GGC  TGG  ACC  GGC  GTC  CGC  GAC  GCC  TCC  GCG  TAT  GGT  CCC  TCG       492
His  Ala  Gly  Trp  Thr  Gly  Val  Arg  Asp  Ala  Ser  Ala  Tyr  Gly  Pro  Ser
                     50                       55                       60

GCG  CCG  CAA  CCC  GTG  GAG  CCT  GGC  GGC  TCG  CCG  ATC  CTT  GGG  ACA  CAC       540
Ala  Pro  Gln  Pro  Val  Glu  Pro  Gly  Gly  Ser  Pro  Ile  Leu  Gly  Thr  His
           65                       70                       75

GGC  GAC  CCT  CCG  TTT  GAC  GAG  GAC  TGC  CTG  ACT  CTC  AAT  CTT  TGG  ACC       588
Gly  Asp  Pro  Pro  Phe  Asp  Glu  Asp  Cys  Leu  Thr  Leu  Asn  Leu  Trp  Thr
                80                       85                       90

CCG  AAC  CTC  GAC  GGC  GGT  AGC  CGG  CCG  GTC  CTC  GTC  TGG  ATC  CAT  GGT       636
Pro  Asn  Leu  Asp  Gly  Gly  Ser  Arg  Pro  Val  Leu  Val  Trp  Ile  His  Gly
      95                      100                      105

GGG  GGC  CTA  CTA  ACC  GGC  TCG  GGA  AAT  CTA  CCT  AAC  TAC  GCG  ACC  GAT       684
Gly  Gly  Leu  Leu  Thr  Gly  Ser  Gly  Asn  Leu  Pro  Asn  Tyr  Ala  Thr  Asp
110                      115                      120                      125

ACC  TTC  GCC  CGC  GAC  GGC  GAC  TTG  GTA  GGT  ATC  TCA  ATC  AAT  TAC  CGG       732
Thr  Phe  Ala  Arg  Asp  Gly  Asp  Leu  Val  Gly  Ile  Ser  Ile  Asn  Tyr  Arg
                     130                      135                      140
```

| | |
|---|---|
| CTC GGG CCT CTT GGA TTC CTC GCA GGA ATG GGC GAC GAG AAT GTC TGG<br>Leu Gly Pro Leu Gly Phe Leu Ala Gly Met Gly Asp Glu Asn Val Trp<br>              145                        150                        155 | 780 |
| CTC ACC GAT CAG GTA GAG GCA CTG CGC TGG ATT GCA GAT AAC GTT GCT<br>Leu Thr Asp Gln Val Glu Ala Leu Arg Trp Ile Ala Asp Asn Val Ala<br>       160                           165                          170 | 828 |
| GCC TTC GGT GGA GAC CCG AAC CGG ATC ACT CTC GTC GGT CAA TCA GGC<br>Ala Phe Gly Gly Asp Pro Asn Arg Ile Thr Leu Val Gly Gln Ser Gly<br>175                              180                          185 | 876 |
| GGG GCA TAC TCG ATC GCA GCG CTC GCC CAA CAC CCG GTC GCC CGT CAG<br>Gly Ala Tyr Ser Ile Ala Ala Leu Ala Gln His Pro Val Ala Arg Gln<br>190                      195                        200                    205 | 924 |
| CTG TTC CAC CGC GCG ATC CTA CAA AGC CCA CCA TTC GGG ATG CAA CCC<br>Leu Phe His Arg Ala Ile Leu Gln Ser Pro Pro Phe Gly Met Gln Pro<br>                      210                          215                        220 | 972 |
| CAT ACA GTT GAA GAA TCG ACG GCA AGG ACG AAG GCC CTG GCC CGG CAT<br>His Thr Val Glu Glu Ser Thr Ala Arg Thr Lys Ala Leu Ala Arg His<br>                          225                      230                        235 | 1020 |
| CTC GGG CAC GAT GAC ATC GAG GCC CTG CGC CAT GAG CCG TGG GAG AGG<br>Leu Gly His Asp Asp Ile Glu Ala Leu Arg His Glu Pro Trp Glu Arg<br>            240                      245                        250 | 1068 |
| CTG ATT CAA GGC ACG ATA GGC GTC CTG ATG GAA CAC ACC AAA TTT GGC<br>Leu Ile Gln Gly Thr Ile Gly Val Leu Met Glu His Thr Lys Phe Gly<br>255                              260                          265 | 1116 |
| GAA TGG CCC CTG GCA TTC TAT CCG GTG TTC GAT GAG GCA ACG ATA CCT<br>Glu Trp Pro Leu Ala Phe Tyr Pro Val Phe Asp Glu Ala Thr Ile Pro<br>270                      275                        280                    285 | 1164 |
| CGC CAT CCG ATT GAG TCC ATT ATC GAT TCC GAC ATC GAA ATC ATC ATC<br>Arg His Pro Ile Glu Ser Ile Ile Asp Ser Asp Ile Glu Ile Ile Ile<br>                      290                          295                        300 | 1212 |
| GGC TGG ACA CGC GAC GAG GGC ACT TTT CCG TTT GCC TTC GAC CCT CAG<br>Gly Trp Thr Arg Asp Glu Gly Thr Phe Pro Phe Ala Phe Asp Pro Gln<br>                305                          310                        315 | 1260 |
| GTT TCA CAG GCG GAT CGC GAT CAG GTC GAG TCA TGG TTG CAG AAG CGT<br>Val Ser Gln Ala Asp Arg Asp Gln Val Glu Ser Trp Leu Gln Lys Arg<br>            320                      325                        330 | 1308 |
| TTC GGA GAC CAC GCC GCC TCG GCC TAC GAG GCT CAC GCC GGC GAC GGA<br>Phe Gly Asp His Ala Ala Ser Ala Tyr Glu Ala His Ala Gly Asp Gly<br>                335                          340                        345 | 1356 |
| ACC AGT CCT TGG ACC GTT ATC GCC AAC GTT GTG GGC GAC GAG CTC TTT<br>Thr Ser Pro Trp Thr Val Ile Ala Asn Val Val Gly Asp Glu Leu Phe<br>350                              355                          360                  365 | 1404 |
| CAC AGC GCT GGG TAC CGG GTC GCG GAC GAA CGG GCA ACG CGC AGA CCG<br>His Ser Ala Gly Tyr Arg Val Ala Asp Glu Arg Ala Thr Arg Arg Pro<br>                        370                          375                      380 | 1452 |
| GTA CGG GCC TAT CAG TTC GAC GTA GTC TCG CCC TTG TCG GAC GGA GCC<br>Val Arg Ala Tyr Gln Phe Asp Val Val Ser Pro Leu Ser Asp Gly Ala<br>                      385                        390                        395 | 1500 |
| CTC GGC GCG GTC CAC TGC ATC GAA ATG CCG TTC ACA TTT GCC AAT CTC<br>Leu Gly Ala Val His Cys Ile Glu Met Pro Phe Thr Phe Ala Asn Leu<br>        400                          405                          410 | 1548 |
| GAC CGT TGG ACG GGG AAG CCG TTC GTG GAC GGC CTG GAT CCA GAC GTG<br>Asp Arg Trp Thr Gly Lys Pro Phe Val Asp Gly Leu Asp Pro Asp Val<br>       415                          420                        425 | 1596 |
| GTG GCT CGG GTG ACC AAC GTG TTG CAT CAG GCC TGG ATC GCA TTC GTC<br>Val Ala Arg Val Thr Asn Val Leu His Gln Ala Trp Ile Ala Phe Val<br>430                              435                          440                  445 | 1644 |
| CGA ACG GGA GAC CCC ACG CAC GAC CAG TTG CCG GTG TGG CCA ACG TTC<br>Arg Thr Gly Asp Pro Thr His Asp Gln Leu Pro Val Trp Pro Thr Phe<br>                      450                          455                        460 | 1692 |

| | | | | | | | | | | | | | | | |
|---|---|---|---|---|---|---|---|---|---|---|---|---|---|---|---|
| CGA | GCG | GAC | GAC | CCA | GCG | GTG | TTG | GTC | GTC | GGC | GAC | GAG | GGA | GCA | GAG | 1740 |
| Arg | Ala | Asp | Asp | Pro | Ala | Val | Leu | Val | Val | Gly | Asp | Glu | Gly | Ala | Glu | |
| | | | 465 | | | | 470 | | | | | | 475 | | | |
| GTG | GCG | CGG | GAT | CTA | GCG | CGC | CCG | GAC | CAC | GTC | AGC | GTT | CGG | ACC | CTA | 1788 |
| Val | Ala | Arg | Asp | Leu | Ala | Arg | Pro | Asp | His | Val | Ser | Val | Arg | Thr | Leu | |
| | | 480 | | | | | 485 | | | | | | 490 | | | |

```
TGAGGGTCGC GGGTCGCCGG GGTCTTGAGG CCGGAGGGCC TCGCGTATGC AGTGATTCGT    1848

GGATCACCGG CCAGTT                                                    1864
```

( 2 ) INFORMATION FOR SEQ ID NO:7:

( i ) SEQUENCE CHARACTERISTICS:
        ( A ) LENGTH: 493 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Ile  Thr  Arg  Pro  Ile  Ala  His  Thr  Thr  Ala  Gly  Asp  Leu  Gly  Gly
 1                  5                      10                      15

Cys  Leu  Glu  Asp  Gly  Leu  Tyr  Val  Phe  Arg  Gly  Val  Pro  Tyr  Ala  Glu
              20                      25                      30

Pro  Pro  Val  Gly  Asp  Leu  Arg  Trp  Arg  Ala  Ala  Arg  Pro  His  Ala  Gly
         35                      40                      45

Trp  Thr  Gly  Val  Arg  Asp  Ala  Ser  Ala  Tyr  Gly  Pro  Ser  Ala  Pro  Gln
     50                      55                      60

Pro  Val  Glu  Pro  Gly  Gly  Ser  Pro  Ile  Leu  Gly  Thr  His  Gly  Asp  Pro
65                      70                      75                      80

Pro  Phe  Asp  Glu  Asp  Cys  Leu  Thr  Leu  Asn  Leu  Trp  Thr  Pro  Asn  Leu
                   85                      90                      95

Asp  Gly  Gly  Ser  Arg  Pro  Val  Leu  Val  Trp  Ile  His  Gly  Gly  Gly  Leu
              100                     105                     110

Leu  Thr  Gly  Ser  Gly  Asn  Leu  Pro  Asn  Tyr  Ala  Thr  Asp  Thr  Phe  Ala
         115                     120                     125

Arg  Asp  Gly  Asp  Leu  Val  Gly  Ile  Ser  Ile  Asn  Tyr  Arg  Leu  Gly  Pro
     130                     135                     140

Leu  Gly  Phe  Leu  Ala  Gly  Met  Gly  Asp  Glu  Asn  Val  Trp  Leu  Thr  Asp
145                     150                     155                     160

Gln  Val  Glu  Ala  Leu  Arg  Trp  Ile  Ala  Asp  Asn  Val  Ala  Ala  Phe  Gly
                   165                     170                     175

Gly  Asp  Pro  Asn  Arg  Ile  Thr  Leu  Val  Gly  Gln  Ser  Gly  Gly  Ala  Tyr
              180                     185                     190

Ser  Ile  Ala  Ala  Leu  Ala  Gln  His  Pro  Val  Ala  Arg  Gln  Leu  Phe  His
         195                     200                     205

Arg  Ala  Ile  Leu  Gln  Ser  Pro  Pro  Phe  Gly  Met  Gln  Pro  His  Thr  Val
     210                     215                     220

Glu  Glu  Ser  Thr  Ala  Arg  Thr  Lys  Ala  Leu  Ala  Arg  His  Leu  Gly  His
225                     230                     235                     240

Asp  Asp  Ile  Glu  Ala  Leu  Arg  His  Glu  Pro  Trp  Glu  Arg  Leu  Ile  Gln
                   245                     250                     255

Gly  Thr  Ile  Gly  Val  Leu  Met  Glu  His  Thr  Lys  Phe  Gly  Glu  Trp  Pro
              260                     265                     270

Leu  Ala  Phe  Tyr  Pro  Val  Phe  Asp  Glu  Ala  Thr  Ile  Pro  Arg  His  Pro
         275                     280                     285

Ile  Glu  Ser  Ile  Ile  Asp  Ser  Asp  Ile  Glu  Ile  Ile  Gly  Trp  Thr
     290                     295                     300
```

Arg Asp Glu Gly Thr Phe Pro Phe Ala Phe Asp Pro Gln Val Ser Gln
305                 310             315

Ala Asp Arg Asp Gln Val Glu Ser Trp Leu Gln Lys Arg Phe Gly Asp
            325             330             335

His Ala Ala Ser Ala Tyr Glu Ala His Ala Gly Asp Gly Thr Ser Pro
            340             345             350

Trp Thr Val Ile Ala Asn Val Val Gly Asp Glu Leu Phe His Ser Ala
        355             360             365

Gly Tyr Arg Val Ala Asp Glu Arg Ala Thr Arg Arg Pro Val Arg Ala
    370             375             380

Tyr Gln Phe Asp Val Val Ser Pro Leu Ser Asp Gly Ala Leu Gly Ala
385             390             395             400

Val His Cys Ile Glu Met Pro Phe Thr Phe Ala Asn Leu Asp Arg Trp
            405             410             415

Thr Gly Lys Pro Phe Val Asp Gly Leu Asp Pro Asp Val Val Ala Arg
            420             425             430

Val Thr Asn Val Leu His Gln Ala Trp Ile Ala Phe Val Arg Thr Gly
        435             440             445

Asp Pro Thr His Asp Gln Leu Pro Val Trp Pro Thr Phe Arg Ala Asp
    450             455             460

Asp Pro Ala Val Leu Val Val Gly Asp Glu Gly Ala Glu Val Ala Arg
465             470             475             480

Asp Leu Ala Arg Pro Asp His Val Ser Val Arg Thr Leu
            485             490

( 2 ) INFORMATION FOR SEQ ID NO:8:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Arthrobacter oxidans
        ( B ) STRAIN: P52

( x i ) SEQUENCE DESCRIPTION: SEQ ID NO:8:

CTAGAGATCT CAACAATGGT TACCAGACCG ATCGCCCACA CCACCGCTGG G     51

( 2 ) INFORMATION FOR SEQ ID NO:9:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

GTCCCCAGCG GTGGTGTGGG CGATCGGTCT GGTAACCATT GTTGAGATC     49